United States Patent
Chu et al.

(10) Patent No.: US 6,503,538 B1
(45) Date of Patent: Jan. 7, 2003

(54) ELASTOMERIC FUNCTIONAL BIODEGRADABLE COPOLYESTER AMIDES AND COPOLYESTER URETHANES

(75) Inventors: Chih-Chang Chu, Ithaca, NY (US); Ramaz Katsarava, Tbilisi, GA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/651,338

(22) Filed: Aug. 30, 2000

(51) Int. Cl.$^7$ .................. A61K 9/16; C08G 69/26
(52) U.S. Cl. .............. 424/497; 528/176; 528/179; 528/182; 528/184; 528/189; 528/332; 528/335; 528/336; 528/339; 524/86; 524/233; 424/426; 424/451; 424/457; 424/489; 424/490
(58) Field of Search ............... 528/176, 179, 528/182, 184, 189, 332, 335, 336, 339; 524/86, 233; 424/426, 451, 457, 489, 490, 497

(56) References Cited

U.S. PATENT DOCUMENTS

| | | | |
|---|---|---|---|
| 5,100,992 A | * 3/1992 | Cohn et al. | 424/501 |
| 5,133,742 A | 7/1992 | Pinchuk | 623/1 |
| 5,485,496 | 1/1996 | Lee et al. | 378/64 |
| 5,516,881 | 5/1996 | Lee et al. | 528/320 |
| 5,610,241 | 3/1997 | Lee et al. | 525/411 |
| 5,721,131 | 2/1998 | Rudolph et al. | 435/240.243 |
| 5,919,893 | * 7/1999 | Roby et al. | 525/411 |

FOREIGN PATENT DOCUMENTS

| | | | |
|---|---|---|---|
| DE | 4224401 A1 | 1/1994 | |
| EP | 0396429 A2 | 11/1990 | |
| SU | 872531 | 10/1981 | C08G/71/04 |
| SU | 876663 | 10/1981 | C08G/63/16 |
| SU | 905228 | 2/1982 | C08G/71/02 |
| SU | 1016314 | 5/1983 | C08G/18/32 |
| SU | 811750 | 9/1983 | C07C/79/18 |
| SU | 1293518 | 2/1987 | G01M/7/00 |
| SU | 790725 | 2/1989 | C08G/73/10 |
| WO | WO 98/32398 | 7/1998 | |

OTHER PUBLICATIONS

Saotome, Y., et al., "Novel Enzymatically Degradable Polymers Comprising α–Amino Acid, 1,2–Ethanediol, and Adipic Acid", *Chemistry Letters*, pp. 21–24, (1991).

* cited by examiner

Primary Examiner—Samuel A. Acquah
(74) *Attorney, Agent, or Firm*—Schwegman, Lundberg, Woessner & Kluth, P.A.

(57) ABSTRACT

The present invention provides elastomeric copolyester amides, elastomeric copolyester urethanes, and methods for making the same. The polymers that are based on α-amino acids and possess suitable physical, chemical and biodegradation properties. The polymers are useful as carriers of drugs or other bioactive substances.

90 Claims, No Drawings

ELASTOMERIC FUNCTIONAL BIODEGRADABLE COPOLYESTER AMIDES AND COPOLYESTER URETHANES

BACKGROUND OF THE INVENTION

While they potentially offer many advantages due to their "organic nature," conventional poly(α-amino acids) possess many undesirable physical, chemical and biodegradation properties. For example, the biological and material properties of conventional poly(α-amino acids) cannot be varied over a wide range. In addition, the synthesis of many conventional poly(α-amino acids) is difficult and expensive.

A considerable amount of attention has therefore been focussed on replacing the amide (peptide) linkage in the conventional poly(α-amino acids) with a variety of non-amide bond to provide novel polymeric systems that are based on α-amino acids. One class of α-amino acid derived polymers are polyisopeptides (alternatively known as pseudo-poly(amino acids)), which belong to the XY-type heterochain polymers. Polyisopeptides are usually foamed by linking trifunctional α-amino acids in the backbone chains. However, relatively few attempts have been made to synthesize polyisopeptides. For example, Sekiguchi et al. obtained poly-β-(α-alkyl-L-aspartate) by the ring-opening polymerization of β-lactams. See, Rodriguez-Galan, A. et al., *Makromol. Chem., Makromol. Symp.*, 6, 277 (1986) and Vives, J. et al., *Makromol. Chem., Rapid Commun.*, 10(1):13 (1989). One major limiting feature of polyisopeptides is that structural modifications are limited solely to chemical variations at the N-acyl residue of the polyisopeptide. This narrow range of chemical modification has resulted in an undesirably narrow range of material properties of these polymers.

Another class of α-amino acid derived polymers are amino acid based bioanalagous polymers (AABBPs), which belong to the XX-YY heterochain polymers. AABBPs are mainly obtained by the polycondensation of XX (one type of monomer having two X functional groups) and YY (another type of monomer having two Y functional groups). AABBPs are not pure polyamino acids or pseudo-polyamino acids because they include residues of other types of monomers (e.g., dicarboxylic acids and diols).

One class of AABBPs are poly(ester ureas) (PEUs), which are prepared from bis-α-aminoacyl diol monomers. The first attempt to use bis-α-aminoacyl(phenylalanyl) diol for preparing bioabsorbable, semi-physiological polymers similar to poly(ester urea) was by Huang et al. Huang S. J., et al., *J. Appl. Polym. Sci.*, 23(2): 429 (1979). Only low-molecular-weight PEUs, having limited material properties, could be prepared by this route.

Lipatova et al. have also synthesized semi-physiological poly(ester urethane ureas) from bis-L-phenylalanyl diols, diols, and diisocyanates. Lipatova T. E., et al., *Dokl. Akad. Nauk SSSR*, 251(2): 368 (1980) and Gladyr I. I., et al. *Vysokomol. Soed.*, 31B(3): 196 (1989). However, no information on the synthesis of the starting material (e.g., α-diamino diesters) was given.

Yoneyama et al. reported on the synthesis of high-molecular-weight semi-physiological PEUs by the interaction of free α-diamino-diesters with non-physiological diisocyanates. Yoneyama M., et al., *Polym. Prepr. Jpn.*, 43(1): 177 (1994). Contrary to Huang et al. (Huang S. J., et al., *J. Appl. Polym. Sci.*, 23(2): 429 (1979)), high-molecular-weight PEUs were obtained in some cases. In view of this preliminary data, there remains an ongoing need for novel polymers based on α-amino acids that possess a wide range of physical, chemical and biodegradation properties.

SUMMARY OF THE INVENTION

The present invention provides polymers that are based on α-amino acids. In contrast to conventional poly(α-amino acids), the polymers of the present invention (e.g., elastomeric functional copolyester amides and copolyester urethanes) possess advantageous physical, chemical and biodegradation properties. For example, the polymers of the present invention possess suitable biodegradation (weight loss percent) properties under varying conditions, (see, Table III). The hydrolysis of the polymers can be catalyzed by hydrolases (e.g., trypsin, α-chymotrypsin, lipase, etc.). As such, the polymers can be used as carriers for covalent immobilization (attachment) of various drugs and other bioactive substances. In addition, the enzyme catalyzed biodegradation rates of the polymer of the present invention can be changed by varying the polymer composition (e.g., l/p ratio) and/or the nature of the functional groups (e.g., dicarboxylic acids, diols, or α-amino acids).

The present invention provides a polymer of formula (VII):

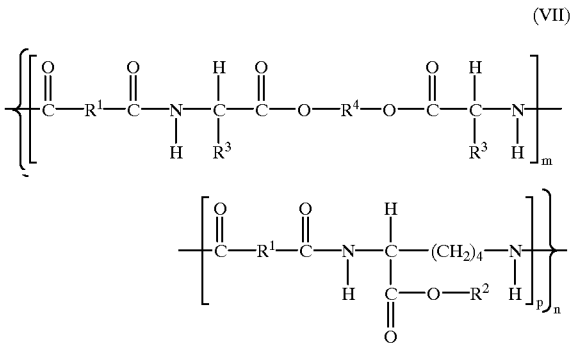

wherein m is about 0.1 to about 0.9;

p is about 0.9 to about 0.1;

n is about 50 to about 150;

each $R^1$ is independently $(C_2-C_{20})$alkylene;

each $R^2$ is independently hydrogen, or $(C_6-C_{10})$aryl $(C_1-C_6)$alkyl;

each $R^3$ is independently hydrogen, $(C_1-C_6)$alkyl, $(C_2-C_6)$alkenyl, $(C_2-C_6)$alkynyl, or $(C_6-C_{10})$aryl $(C_1-C_6)$alkyl; and each $R^4$ is independently $(C_2-C_{20})$alkylene; comprising one or more subunits of the formula (I):

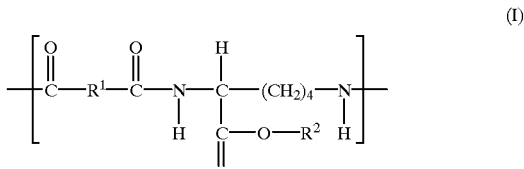

and one or more subunits of the formula (II):

(II)

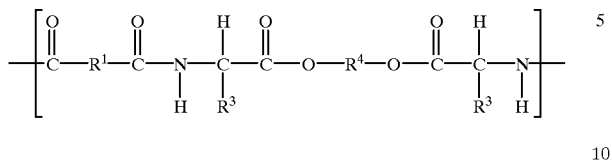

wherein
the combined number of subunits (I) and (II) is about 50 to about 150.

Specifically, each $R^1$ can independently be $(CH_2)_4$, $(CH_2)_8$, or $(CH_2)_{12}$; $R^2$ can independently be hydrogen or benzyl; each $R^3$ can independently be iso-butyl or benzyl; and $R^4$ can independently be $(CH_2)_4$, $(CH_2)_6$, $(CH_2)_8$, or $(CH_2)_{12}$.

The present invention also provides a polymer of formula (VII):

(VII)

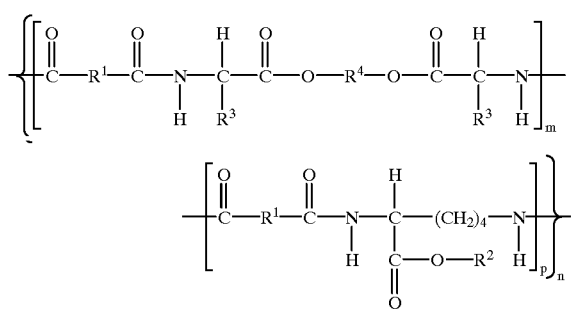

wherein
m is about 0.1 to about 0.9;
p is about 0.9 to about 0.1;
n is about 50 to about 150;
each $R^1$ is independently $(C_2-C_{20})$alkylene;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
each $R^4$ is independently $(C_2-C_{20})$alkylene.

Specifically, each $R^1$ can independently be $(CH_2)_4$, $(CH_2)_8$, or $(CH_2)_{12}$; each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; p/(p+m) can be about 0.9 to about 0.1; and m/(p+m) can be about 0.1 to about 0.9.

The present invention also provides a polymer of formula (VII) formed from an amount of one or more compounds of formula (III):

(III)

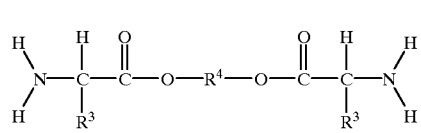

wherein
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and $R^4$ is independently $(C_2-C_{20})$alkylene; or a suitable salt thereof; and an amount of one or more compounds of formula (IV):

(IV)

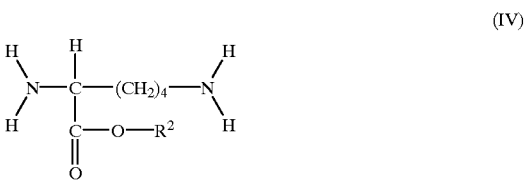

wherein
$R^2$ is independently hydrogen, or $(C_6-C_{10})$aryl$(C_1-C_6)$alkyl; or a suitable salt thereof; and
an amount of one or more compounds of formula (V):

(V)

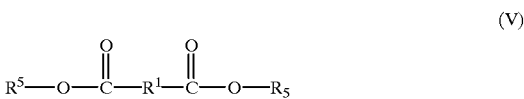

wherein
$R^1$ is independently $(C_2-C_{20})$alkylene; and
each $R^5$ is independently $(C_6-C_{10})$aryl, optionally substituted with one or more nitro, cyano, halo, trifluoromethyl, or trifluoromethoxy.

Specifically, $R^1$ can independently be $(CH_2)_4$, $(CH_2)_8$, or $(CH_2)_{12}$; $R^2$ can independently be hydrogen or benzyl; each $R^3$ can independently be iso-butyl or benzyl; $R^4$ can independently be $(CH_2)_4$, $(CH_2)_6$, $(CH_2)_8$, or $(CH_2)_{12}$; each $R^5$ can independently be p-nitrophenyl; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester; and the compound of formula (V) can be di-p-nitrophenyl adipate, di-p-nitrophenyl sebacinate, or di-p-nitrophenyl dodecyldicarboxylate.

The present invention also provides a method for preparing a polymer of formula (VII):

(VII)

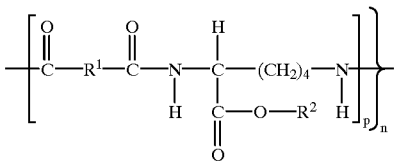

wherein
m is about 0.1 to about 0.9;
p is about 0.9 to about 0.1;
n is about 50 to about 150;
each $R^1$ is independently $(C_2-C_{20})$alkylene;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and each $R^4$ is independently $(C_2–C_{20})$alkylene; comprising contacting an amount of one or more compounds of formula (III):

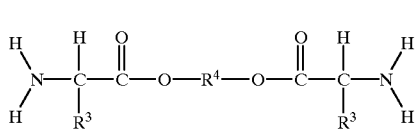
(III)

or a suitable salt thereof; and an amount of one or more compounds of formula (IV):

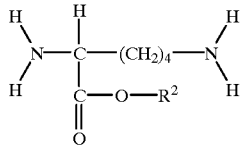
(IV)

or a suitable salt thereof; and
an amount of one or more compounds of formula (V):

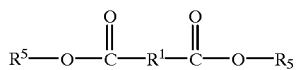
(V)

wherein
each $R^5$ is independently $(C_6–C_{10})$aryl optionally substituted with one or more nitro, cyano, halo, trifluoromethyl, or trifluoromethoxy;
under suitable conditions to provide the polymer of formula (VII).

Specifically, each $R^1$ can independently be $(CH_2)_4$, $(CH_2)_8$, or $(CH_2)_{12}$; each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^5$ can be p-nitrophenyl; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester; the compound of formula (V) can be di-p-nitrophenyl adipate, di-p-nitrophenyl sebacinate, or di-p-nitrophenyl dodecyldicarboxylate; p/(p+m) can be about 0.9 to about 0.1; and m/(p+m) can be about 0.1 to about 0.9. The contacting can be carried out in the presence of a base, wherein the base can be triethylamine. The contacting can also be carried out in the present, of a solvent, wherein the solvent can be N,N-dimethylacetamide. The contacting can also be carried out at a temperature of about 50° C. to about 100° C. The contacting can preferably occur for about 10 hours to about 24 hours. The polymer of formula (VII) can also optionally be purified.

The present invention also provides a polymer of formula (XI):

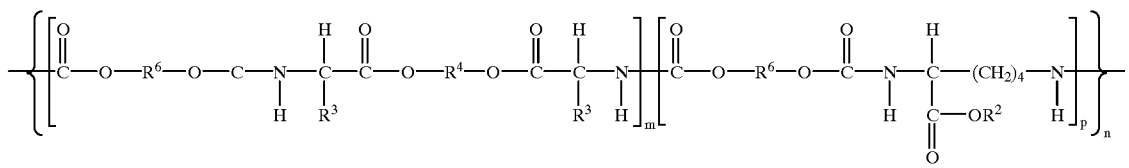
(XI)

wherein m is about 0.1 to about 0.9;

p is about 0.9 to about 0.1;

n is about 50 to about 150;

each $R^2$ is independently hydrogen, or $(C_6–C_{10})$aryl $(C_1–C_6)$alkyl;

each $R^3$ is independently hydrogen, $(C_1–C_6)$alkyl, $(C_2–C_6)$alkenyl, $(C_2–C_6)$alkynyl, or $(C_6–C_{10})$aryl $(C_1–C_6)$alkyl;

each $R^4$ is independently $(C_2–C_{20})$alkylene; and each $R^6$ is independently $(C_1–C_{20})$alkylene or $(C_2–C_8)$ alkyloxy$(C_2–C_{20})$alkylene;

comprising one or more subunits of the formula (VIII):

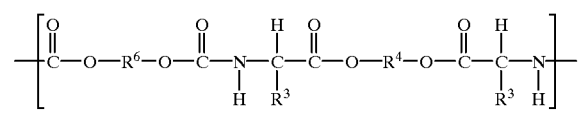
(VIII)

wherein each $R^3$ is independently hydrogen, $(C_1–C_6)$alkyl, $(C_2–C_6)$alkenyl, $(C_2–C_6)$alkynyl, or $(C_6–C_{10})$aryl $(C_1–C_6)$alkyl; and $R^4$ is independently $(C_2–C_{20})$alkylene;

$R^6$ is independently $(C_2–C_{20})$alkylene or $(C_2–C_8)$ alkyloxy$(C_2–C_{20})$alkylene; and one or more subunits of the formula (IX):

$$\left[\begin{array}{c}O\\\|\\C-O-R^6-O-C-N-C-(CH_2)_4-N\\\|\\H\end{array}\right.\left.\begin{array}{c}O\quad H\\\|\\\\\\C-OR^2\\\|\\O\end{array}\right.\left.\begin{array}{c}\\\\H\end{array}\right]$$ (IX)

wherein the total number of subunits (VIII) and (IV) is about 50 to about 150;

$R^2$ is independently hydrogen, or $(C_6-C_{10})$aryl$(C_1-C_6)$ alkyl.

Specifically, $R^2$ can independently be hydrogen or benzyl; each $R^3$ can independently be iso-butyl or benzyl; $R^4$ can independently be $(CH_2)_4$, $(CH_2)_6$, $(CH_2)_8$ or $(CH_2)_{12}$; and $R^6$ can independently be $(CH_2)_3$ or $(CH_2)_2-O-(CH_2)_2$.

The present invention also provides a polymer of formula (XI):

$$\left\{\left[\begin{array}{c}O\\\|\\C-O-R^6-O-C-N-C-C-O-R^4-O-C-C-N\\\|\\H\quad R^3\end{array}\right.\left.\begin{array}{c}O\quad H\\\|\\\\R^3\quad H\end{array}\right]_m\left[\begin{array}{c}O\\\|\\C-O-R^6-O-C-N-C-(CH_2)_4-N\\\|\\H\quad C-OR^2\\\|\\O\end{array}\right.\left.\begin{array}{c}\\\\H\end{array}\right]_p\right\}_n$$ (XI)

wherein m is about 0.1 to about 0.9;

p is about 0.9 to about 0.1;

n is about 50 to about 150;

each $R^2$ is independently hydrogen, or $(C_6-C_{10})$aryl $(C_1-C_6)$alkyl;

each $R^3$ is independently hydrogen, $(C_1-C_6)$alkyl, $(C_2-C_6)$alkenyl, $(C_2-C_6)$alkynyl, or $(C_6-C_{10})$aryl $(C_1-C_6)$alkyl;

each $R^4$ is independently $(C_2-C_{20})$alkylene; and each $R^6$ is independently $(C_2-C_{20})$alkylene or $(C_2-C_8)$ alkyloxy$(C_2-C_{20})$alkylene.

Specifically, each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^6$ can independently be $(CH_2)_3$ or $(CH_2)_2-$ $O-(CH_2)_2$; p/(p+m) can be about 0.9 to about 0.1; and m/(p+m) can be about 0.1 to about 0.9.

The present invention also provides a polymer of formula (XI) formed from an amount of one or more compounds of formula (III):

$$\begin{array}{c}H\quad H\quad O\quad\quad\quad\quad O\quad H\quad H\\\\N-C-C-O-R^4-O-C-C-N\\\\H\quad R^3\quad\quad\quad\quad\quad R^3\quad H\end{array}$$ (III)

wherein each $R^3$ is independently hydrogen, $(C_1-C_6)$alkyl, $(C_2-C_6)$alkenyl, $(C_1-C_6)$alkynyl, or $(C_6-C_{10})$aryl$(C_1-C_6)$ alkyl; and $R^4$ is independently $(C_2-C_{20})$alkylene; or a suitable salt thereof; and an amount of one or more compounds of formula (IV):

$$\begin{array}{c}H\quad H\quad\quad\quad\quad\quad H\\\\N-C-(CH_2)_4-N\\\\H\quad C-O-R^2\quad H\\\quad\|\\\quad O\end{array}$$ (IV)

wherein $R^2$ is independently hydrogen, or $(C_6-C_{10})$aryl$(C_1-C_6)$ alkyl; or a suitable salt thereof, and an amount of one or more compounds of formula (X):

$$R^5-O-\overset{O}{\underset{\|}{C}}-O-R^6-O-\overset{O}{\underset{\|}{C}}-O-R^5$$ (X)

wherein each $R^5$ is independently $(C_1-C_{10})$aryl optionally substituted with one or more nitro, cyano, halo, trifluoromethyl, or trifluoromethoxy; and $R^6$ is independently $(C_2-C_{20})$alkylene or $(C_2-C_8)$ alkyloxy$(C_2-C_{20})$alkylene.

Specifically, $R^2$ can independently be hydrogen or benzyl; each $R^3$ can independently be iso-butyl or benzyl; $R^4$ can independently be $(CH_2)_4$, $(CH_2)_6$, $(CH_2)_8$, or $(CH_2)_{12}$; each $R^5$ can be p-nitrophenyl; $R^6$ can independently be $(CH_2)_3$ or $(CH_2)_2-O-(CH_2)_2$; the compound of formula (III) can be the di-p-toluenesulfonic acid salt of a bis-(L-α-amino acid)-α,ω-alkylene diester; the compound of formula (IV) can be the di-p-toluenesulfonic acid salt of L-lysine benzyl ester; the compound of formula (X) can be 1,3-bis(4-nitrophenoxycarbonyloxy)propane; or 2,2'-bis-4-nitrophenoxycarbonyloxy ethylether; p/(p+m) can be about 0.9 to about 0.1; and m/(p+m) can be about 0.1 to about 0.9.

The present invention also provides a method for preparing a polymer of formula (XI):

(XI)

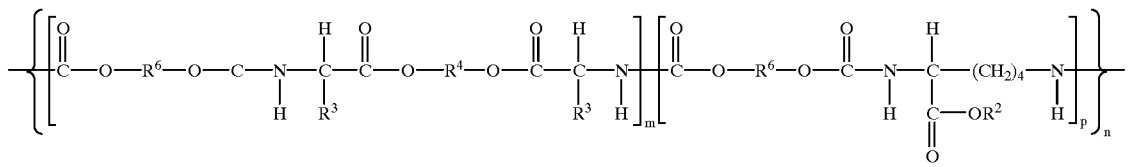

wherein
is about 0.1 to about 0.9;
p is about 0.9 to about 0.1;
n is about 50 to about 150;
each $R^2$ is independently hydrogen or $(C_6–C_{10})$aryl $(C_1–C_6)$alkyl;
each $R^3$ is independently hydrogen, $(C_1–C_6)$alkyl, $(C_2–C_6)$alkenyl, $(C_2–C_6)$alkynyl, or $(C_6–C_{10})$aryl $(C_1–C_6)$alkyl;
each $R^4$ is independently $(C_2–C_{20})$alkylene;
each $R^5$ is independently $(C_6–C_{10})$aryl optionally substituted with one or more nitro, cyano, halo, trifluoromethyl, or trifluoromethoxy; and
each $R^6$ is independently $(C_2–C_{20})$alkylene or $(C_2–C_8)$alkyloxy$(C_2–C_{20})$alkylene;
comprising contacting an amount of one or more compounds of formula (III):

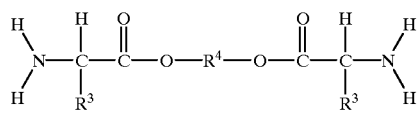

(III)

or a suitable salt thereof; and
an amount of one or more compounds of formula (IV):

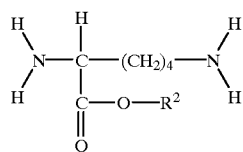

(IV)

or a suitable salt thereof; and
an amount of one or more compounds of formula (X):

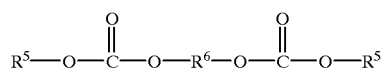

(X)

under suitable conditions to provide the polymer of formula (XI).

Specifically, each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^5$ can be p-nitrophenyl; each $R^6$ can independently be $(CH_2)_3$ or $(CH_2)_2$—O—$(CH_2)_2$; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester; the compound of formula (X) can be 1,3-bis(4-nitro-phenoxycarbonyloxy)propane, or 2,2'-bis-4-nitrophenoxycarbonyloxy ethylether; p/(p+m) can be about 0.9 to about 0.1; and m/(p+m) can be about 0.1 to about 0.9. The contacting can be carried out in the presence of a base, wherein the base can be triethylamine. The contacting can be carried out in the presence of a solvent, wherein the solvent can be N,N-dimethylacetamide. The contacting can be carried out at a temperature of about 50° C. to about 100° C. The contacting can occur for about 10 hours to about 24 hours. In addition, the polymer of formula (XI) can optionally be purified.

The biodegradation of the copolyester amides and copolyester urethanes of the present invention allows the delivery of essential α-amino acids to targeted sites (e.g., to facilitate wound repair of injured tissues). In addition, the polymers of the present invention can be used for the attachment free iminoxyl radicals for suppressing inconsolable cell proliferation, and heparin or hirudin for increasing hemocompatibility. These modified polymers can be used to coat stents to suppress restenosis. In addition, the polymers of the present invention can be used as polyacids for the application in gynecology as impregnated contraceptive agents, e.g., for the controlled release of ferrous gluconate and the like. Furthermore, the polymers of the present invention can be used as polyacids for the attachment of unsaturated compounds, e.g., allyl amine or allyl alcohol, to obtain photo-curable and cross-linkable biodegradable polymers. The present polymers can be cross-linked with other polymers containing double bonds to create hybrid materials.

The biological and material properties of the polymers of the present invention can be varied over a wide range because the polymers can be formed from starting materials having varying functional groups (e.g., dicarboxylic acids, diols, and α-amino acids). See, e.g., Examples 1–22. In contrast to conventional poly(α-amino acids), the elastomeric functional copolyester amides and copolyester urethanes of the present invention can be obtained in high yields. See, Table III. For example, the compounds of the present invention can be prepared in yields up to about 97%. In addition, the reaction conditions employed to prepare the polymers of the present invention are relatively simple and the reagents are relatively inexpensive.

DETAILED DESCRIPTION OF THE INVENTION

The following definitions are used, unless otherwise described: halo can be chloro, fluoro, bromo, or iodo. Alkyl, alkenyl, alkynyl, etc. denote both straight and branched groups; but reference to an individual radical such as "propyl" embraces only the straight chain radical, a branched chain isomer such as "isopropyl" being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific and preferred values listed below for radicals, substituents, and ranges, are for illustration only; they do not exclude other defined values or other values within defined ranges for the radicals and substituents As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Alkylene" is intended to include both branched and straight-chain saturated aliphatic hydrocarbon groups having two open valences and having the specified number of carbon atoms. Examples of alkylene include, but are not limited to, methylene, ethylene, n-propylene, n-butylene, s-butylene, and n-pentylene. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Alkenyl" is intended to include hydrocarbon chains of either a straight or branched configuration having one or more unsaturated carbon-carbon bonds, which may occur in any stable point along the chain, such as ethenyl and propenyl. "Alkynyl" is intended to include hydrocarbon chains of either a straight or branched configuration having one or more triple carbon-carbon bonds, which may occur in any stable point along the chain, such as ethynyl and propynyl. "Aryl" denotes a phenyl radical or an ortho-fused bicyclic carbocyclic radical having about nine to ten ring atoms in which at least one ring is aromatic. Examples of aryl include, but are not limited to phenyl and naphthyl.

A specific value for $R^1$ is $(CH_2)_4$, $(CH_2)_8$, or $(CH_2)_{12}$.

A specific value for $R^2$ is hydrogen, benzyl, sec-phenethyl, or methylbenzyl. Another specific value for $R^2$ is benzyl.

A specific value for $R^3$ is iso-butyl or benzyl.

A specific value for $R^4$ is $(CH_2)_4$, $(CH_2)_6$, $(CH_2)_8$, or $(CH_2)_{12}$.

A specific value for $R^5$ is p-nitrophenyl.

A specific value for $R^6$ is $(CH_2)_3$ or $(CH_2)_2$—O—$(CH_2)_2$.

A specific value for m is about 0.25 to about 0.75.

A specific value for p is about 0.75 to about 0.25.

A specific value for n is about 75 to about 125.

A specific value for p/(p+m) is about 0.75 to about 0.25.

A specific value for m/(p+m) is about 0.25 to about 0.75.

A specific value for (p+m) is about 0.9 to about 1.1. Another specific value for (p+m) is about 0.75 to about 1.25.

A specific group of compounds of formula (III) are the di-p-tolunesulfonic acid salts of a bis-(L-α-amino acid)-α,ω-alkylene diester:

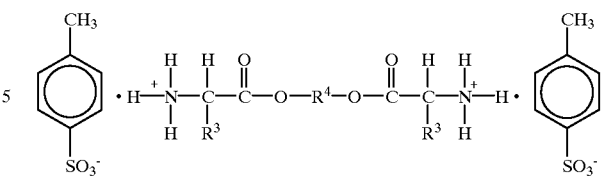

wherein
each $R^3$ is independently is iso-butyl or benzyl; and
$R^4$ is $(CH_2)_4$, $(CH_2)_6$, or $(CH_2)_{12}$.

A specific group of compounds of formula (IV) are the di-p-tolunesulfonic acid salts of L-lysine arylalkyl esters:

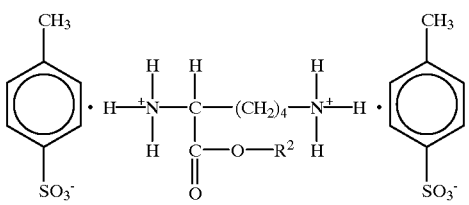

wherein
$R^2$ is benzyl sec-phenethyl, or methylbenzyl. More specifically, $R^2$ can be benzyl.

A specific group of compounds of formula (V) are compounds of the formula:

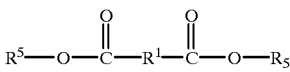

wherein
$R^1$ is $(CH_2)_4$, $(CH_2)_8$, or $(CH_2)_{12}$; and
$R^5$ is p-nitrophenyl.

For example, a specific group of compounds of formula (V) are di-p-nitrophenyl adipate, di-p-nitrophenyl sebacinate, and di-p-nitrophenyl dodecyldicarboxylate A specific group of compounds of formula (X) are compounds of the formula:

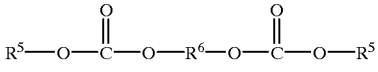

wherein
$R^5$ is p-nitrophenyl; and
$R^6$ is $(CH_2)_3$ or $(CH_2)_2$—O—$(CH_2)_2$.

For example, a specific group of compounds of formula (X) are 1,3-bis(4-nitro-phenoxycarbonyloxy)propane and 2,2'-bis-4-(nitrophenoxycarbonyloxy)ethylether.

In cases where compounds (e.g., starting materials) are sufficiently basic or acidic to form stable nontoxic acid or base salts, the compounds can exist as the acceptable salt. Examples of acceptable salts are organic acid addition salts formed with acids which form an acceptable anion, for example, tosylate, methanesulfonate, acetate, citrate, malonate, tartarate, succinate, benzoate, ascorbate, α-ketoglutarate, and α-glycerophosplhate. Suitable inorganic salts may also exist, including hydrochloride, sulfate, nitrate, bicarbonate, and carbonate salts.

Acceptable salts may be obtained by using standard procedures that are well known in the art, for example by reacting a sufficiently basic compound such as an amine with a suitable acid affording an acceptable anion. Alkali metal (for example, sodium, potassium or lithium) or alkaline earth metal (for example calcium) salts of carboxylic acids can also be made.

Processes for preparing polymers of the present invention (e.g., polymers of formula (VII) and polymers of formula (XI)) are provided as further embodiments of the invention and are as illustrated by the procedures herein below in which the meanings of the generic radicals are as given above unless otherwise qualified.

A polymer of formula (VII) can include one or more subunits of formula (I) and one or more subunits of formula (II). As such, a polymer of formula (VII) can be prepared from a compound of formula (III), from a compound of formula (IV), and from a compound of formula (V). Specifically, a polymer of formula (VII) can be prepared by contacting a compound of formula (III), a compound of formula (IV), and a compound of formula (V) under suitable conditions to provide a polymer of formula (VII).

The compounds of formula (III), (IV), and (V) can be contacted in the presence of a solvent. Any suitable solvent can be employed. When the compounds of formula (III), (IV), and (V) are contacted in the presence of a solvent, the compounds of formula (III), (IV), and (V) are preferably soluble in the solvent. One exemplary suitable solvent is N,N-dimethylacetamide.

The compounds of formula (III), (IV), and (V) can be contacted in the presence of base. Any suitable base can be employed. When the compounds of formula (III), (IV), and (V) are contacted in the presence of a base, the base will preferably adjust the initial pH of the reaction mixture (i.e., the solution including the compounds of formula (III), (IV), and (V)) above about 7. The base is useful to yield the free amines of the compound of formula (III) and the compound of formula (IV). One exemplary suitable base is triethylamine.

The compounds of formula (III), (IV), and (V) can be contacted for a period of time sufficient to provide the polymer of formula (II). For example, the period of time can be from about 1 hour to about 48 hours, inclusive. Preferably, the period of time can be from about 5 hours to about 30 hours, inclusive. More preferably, the period of time can be from about 10 hours to about 24 hours, inclusive.

The compounds of formula (III), (IV), and (V) can be contacted at a temperature sufficient to provide the polymer of formula (VII). For example, the temperature can be from the freezing point of the liquid reaction mixture (e.g., the solvent, base, and the compounds of formula (III), (IV), and (V)) up to about the reflux temperature of the reaction mixture. Preferably, the temperature can be from about 25° C. to about 150° C. More preferably, the temperature can be from about 50° C. to about 100° C.

A polymer of formula (XI) can include one or more subunits of formula (VIII) and one or more subunits of formula (IX). As such, a polymer of formula (XI) can be prepared from a compound of formula (III), from a compound of formula (IV), and from a compound of formula (X). Specifically, a polymer of formula (XI) can be prepared by contacting a compound of formula (III), a compound of formula (IV), and a compound of formula (X) under suitable conditions to provide a polymer of formula (XI).

The compounds of formula (III), (IV), and (X) can be contacted in the presence of a solvent. Any suitable solvent can be employed. When the compounds of formula (III), (IV), and (X) are contacted in the presence of a solvent, the compounds of formula (III), (IV), and (X) are preferably soluble in the solvent. One exemplary suitable solvent is N,N-dimethylacetamide.

The compounds of formula (III), (IV), and (X) can be contacted in the presence of a base. Any suitable base can be employed. When the compounds of formula (III), (IV), and (X) a, contacted in the presence of a base, the base will preferably adjust the initial pH of the reaction mixture (i.e., the solution including the compounds of formula (III), (IV), and (X)) above about 7. The base is useful to yield the free amines of the compound of formula (III) and the compound of formula (IV). One exemplary suitable base is triethylamine.

The compounds of formula (III), (IV), and (X) can be contacted for a period of time sufficient to provide the polymer of formula (VII). For example, the period of time can be from about 1 hour to about 48 hours, inclusive. Preferably, the period of time can be from about 5 hour; to about 30 hours, inclusive. More preferably, the period of time can be from about 10 hours to about 24 hours, inclusive.

The compounds of formula (III), (IV), and (X) can be contacted at a temperature sufficient to provide the polymer of formula (VII). For example, the temperature can be from about the freezing point of the liquid reaction mixture (e.g., the solvent, base, and the compounds of formula (III), (IV), and (X)) up to about the reflux temperature of the reaction mixture. Preferably, the temperature can be from about 25° C. to about 150° C. More preferably, the temperature can be from about 50° C. to about 100° C.

The present invention will now be illustrated by the following non-limiting examples.

EXAMPLES

Preparation of copoly(ester amide)s (coPEAs) and copoly (ester urethane)s (coPEURs) (general procedure)

Dry triethylamine (Net$_3$) (30.8 mL, 0.22 mole) was added to a mixture of predetermined quantities of the di-p-toluenesulfonic acid salt of bis-(L-α-amino acid)α,ω-alkylene diester (III) and the di-p-toluenesulfonic acid salt of L-lysine benzyl ester (IV) (total amount of (III)+(IV)=0.1 mole), and active diester (V) or active bis-carbonate (IV) (0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into cool water. The separated polymer was thoroughly washed with water, dried at about 30° C. under reduced pressure (for final purification of coPEAs and coPEURs see below). Reduced viscosity data ($\eta_{red}$) of the polymers were obtained in m-cresol at a concentration of 0.5 g/dL and t=25° C.

Preparation of Co-PEAs

EXAMPLE 1

Preparation of co-poly-{[N,N'-adipoyl-bis-(L-leucine)-1,6-hexylene diester]}$_{0.75}$-{[N,N'-adipoyl-L-lysine benzyl ester]$_{0.25}$} (1) (compound of formula (VII) wherein m=0.75, p=0.25, n=75, $R_1$=(CH$_2$)$_4$, $R_2$=Bz, $R_3$=iso-butyl, and $R_4$=(CH$_2$)$_6$).

Dry triethylamine (30.8 mL, 0.22 mole) was added to the mixture of the di-p-toluenesulfonic acid salt of bis-(L-leucine)-1,6-hexylene diester (III, $R^4$=(CH$_2$)$_6$) (50.168 g, 0.075 mole); the di-p-toluenesulfonic acid salt of L-lysine benzyl ester (IV) (total amount of (III)+(IV)=0.1 mole) (14.518 g, 0.025 mole); and di-p-nitrophenyl adipate (V, $R^1=(CH_2)_4$) (38.83 g, 0.1 mole) in dry N,N-dimethylacetamide (52.5 mL) (total volume of DMA and $NEt_3$ is 83.3 ml, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 90%, $\eta_{red}$=1.30 dL/g. Mw=32,100, Mn=27,000, Mw/Mn=1.19 (GPC in THF).

EXAMPLE 2

Preparation of co-poly-{[N,N'-sebacoyl-bis-(L-leucine)-1,6-hexylene diester]}$_{0.75}$-{[N,N'-sebacoyl-L-lysine benzyl ester]$_{0.25}$} (2) (compound of formula (VII) wherein m=0.75, p=0.25, n=65, $R_1=(CH_2)_8$, $R_2$=Bz, $R_3$=iso-butyl, and $R_4=(CH_2)_6$).

Dry triethylamine (30.8 mL, 0.22 mole) was added to the mixture of di-p-toluenesulfonic acid salt of bis-(L-leucine)-1,6-hexylene diester (III, $R^4=(CH_2)_6$)(50.168 g (0.075 mole); the di-p-toluenesulfonic acid salt of L-lysine benzyl ester (IV) (14.518 g, 0.025 mole) (total amount of (III)+(IV)=0.1 mole), and di-p-nitrophenyl sebacinate (V, $R^1=(CH_2)_8$) (44.444 g, 0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 91%, $\eta_{red}$=1.40 dL/g. Mw=31.300, Mn=21.000, Mw/Mn=1.49 (GPC in THF). Biodegradation (weight loss in %) at 37° C. after 120 h in phosphate buffer (pH 7.4):~0% weight loss in pure buffer, 1–2% in the buffer with α-chymotrypsin (4 mg/10 mL of buffer), 1–2% in the buffer with lipase (4 mg/10 mL of buffer).

EXAMPLE 3

Preparation of co-poly-{[N,N'-adipoyl-bis-(L-leucine-1,6-hexylene diester]}$_{0.50}$-[N,N'-adipoyl-bis-(L-phenylalanine)-1,6-hexylene diester]$_{0.25}$-{[N,N'-adipoyl-L-lysine benzyl ester]$_{0.25}$} (3) (compound of formula (VII) wherein m=0.50, p=0.50, $R_1=(CH_2)_4$, $R_2$=Bz, $R_3$=iso-butyl and Bz, and $R_4=(CH_2)_6$ and Bz).

Dry triethylamine (30.8 mL, 0.22 mole) was added to the mixture of the di-p-toluenesulfonic acid salt of bis-(L-leucine)-1,6-hexylene diester (III, $R^4=(CH_2)_6$) (34.446 g, 0.050 mole), the di-p-toluenesulfonic acid salt of bis-(L-phenylalanine)1,6-hexylene diester (III, $R^4=CH_2Ph$) (18.924 g, 0.025 mole), the di-p-toluenesulfonic acid salt of L-lysine benzyl ester (IV) (14.5180 g, 0.025 mole) (total amount of (III)+(IV)=0.1 mole), and di-p-nitrophenyl adipate (V, $R^1=(CH_2)_4$) (38.833, 0.1 mole) in dry N,N-dimethylacetamide (DMA) (52.5 mL of) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 94%, $\eta_{red}$=1.40 dL/g. Biodegradation (weight loss in %) at 37° C. after 120 h in phosphate buffer (pH 7.4):~0% in pure buffer, 10% in the buffer with α-chymotrypsin (4 mg/10 mL of buffer), and 35% in the buffer with lipase (4 mg/10 mL of buffer).

EXAMPLE 4

Preparation of co-poly-{[N,N'-sebacoyl-bis-(L-leucine)-1,6-hexylene diester]}$_{0.50}$-[N,N'-sebacoyl-(bis-(L-phenylalanine)-1,6-hexylene diester]$_{0.25}$-{[N,N'-sebacoyl-L-lysine benzyl ester]$_{0.25}$} (4) (compound of formula (VII) wherein $m^1$=0.50, $m^2$=0.25, p=0.25, $R^1=(CH_2)_8$, $R_2$=Bz, $R_3$=iso-butyl, and $R_4=(CH_2)_6$).

Dry triethylamine (30.8 mL, 0.22 mole) was added to the mixture of the of di-p-toluenesulfonic acid salt of bis-(L-leucine)-1,6-hexylene diester (III, $R^4=(CH_2)_6$) (34.446 g, 0.0050 mole), the di-p-toluenesulfonic acid salt of bis-(L-phenylalanine)1,6-hexylene diester (III, $R^4=CH_2Ph$) (18.924 g, 0.025 mole), the di-p-toluenesulfonic acid salt of L-lysine benzyl ester (IV) (14.518 g, 0.025 mole) (total amount of (III)+(IV)=0.1 mole), and di-p-nitrophenyl sebacinate (V, $R^1=(CH_2)_8$) (44.444 g, 0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 95%, $\eta_{red}$=0.77 dL/g. Tg=20.6° C. (DSC).

EXAMPLE 5

Preparation of co-poly-{[N,N'-adipoyl-bis-(L-leucine)-1,6-hexylene diester]}$_{0.50}$-{[N,N'-adipoyl-L-lysine benzyl ester]$_{0.50}$} (5) (compound of formula (VII) wherein m=0.50, p=0.50, $R_1=(CH_2)_4$, $R_2$=Bz, $R_3$=iso-butyl, and $R_4=(CH_2)_6$).

Dry triethylamine (30.8 mL, 0.22 mole) was added to the mixture of the di-p-toluenesulfonic acid salt of bis-(L-leucine)-1,6-hexylene diester (III, $R^4=(CH_2)_6$) (34.446 g, 0.050 mole), the di-p-toluenesulfonic acid salt of L-lysine benzyl ester (IV) (29.036 g, 0.050 mole) (total amount of (III)+(IV)=0.1 mole), and di-p-nitrophenyl adipate (V, $R^1=(CH_2)_4$) (38.833 g, 0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 93%, $\eta^{red}$=1.25 dL/g.

EXAMPLE 6

Preparation of co-poly-{[N,N'-sebacoyl-bis-(L-leucine)-1,6-hexylene diester]}$_{0.50}$-{[N,N'-sebacoyl-L-lysine benzyl ester]$_{0.50}$} (6) (compound of formula (VII) wherein m=0.50, p=0.50, R$_1$=(CH$_2$)$_8$, R$_2$=Bz, R$_3$=iso-butyl, and R$_4$=(CH$_2$)$_6$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (34.446 g, 0.050 mole), the di-p-toluenesulfonic acid salt of L-lysine benzyl ester (IV) (29.036 g, 0.050 mole) (total amount of (III)+(IV)=0.1 mole), and di-p-nitrophenyl sebacinate (V, R$^1$=(CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on nitrophenol and p-toluenesulfonic acid (see below) yield is 95%, $\eta_{red}$=1.31 dL/g.

EXAMPLE 7

Preparation of co-poly-{[N,N'-adipoyl-bis-(L-leucine)-1, 8-octylene diester]}$_{0.90}$-{[N,N'-adipoyl-L-lysine benzyl ester]$_{0.10}$} (7) (compound of formula (VII) wherein m=0.90, p=0.10, R$_1$=(CH$_2$)$_4$, R$_2$=Bz, R$_3$=iso-butyl, and R$_4$=(CH$_2$)$_8$).

Dry triethylamine (30.8 mL, 0.22 mole) was added to the mixture of the di-p-toluenesulfonic acid salt of bis-(L-leucine)-1,8-octylene diester (III, R$^4$=(CH$_2$)$_8$) (64.526 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl adipate (V, R$^1$=(CH$_2$)$_4$) (38.833, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 94%, $\eta_{red}$=1.21 dL/g.

EXAMPLE 8

Preparation of co-poly-{[N,N'-sebacoyl-bis-(L-leucine)-1,4-butylene diester]}$_{0.90}$-{[N,N'-sebacoyl-L-lysine benzyl ester]$_{0.10}$} (8) (compound of formula (VII) wherein m=0.90, p=0.10, R$_1$=(CH$_2$)$_8$, R$_2$=Bz, R$_3$=iso-butyl, and R$_4$=(CH$_2$)$_4$).

Dry triethylamine (30.8 mL, 0.22 mole) was added to the mixture of the di-p-toluenesulfonic acid salt of bis-(L-leucine)-1,4-butylene diester (III, R$^4$=(CH$_2$)$_4$) (59.477 g, 0.090 mole), the di-p-toluenesulfonic acid salt of L-lysine benzyl ester (IV) (5.807 g, 0.010 mole (total amount of (III)+(IV)=0.1 mole), and di-p-nitrophenyl sebacinate (V, R$^1$=(CH$_2$)$_8$) (44.444 g, 0.1 mole) in dry N,N-dimethylacetamide (DMA) (52.5 mL of) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at 30° C. under reduced pressure. After final purification up to nega- tive test on p-nitrophenol and p-toluenesulfonic acid (see below) yield is 95%, $\eta_{red}$=1.28 dL/g.

EXAMPLE 9

Preparation of co-poly-{[N,N'-sebacoyl-bis-(L-leucine)-1,6-hexylene diester]}$_{0.90}$-{[N,N'-sebacoyl-L-lysine benzyl ester]$_{0.10}$} (9) (compound of formula (VII) wherein m=0.90, p=0.10, R$_1$=(CH$_2$)$_8$, R$_2$=Bz, R$_3$=iso-butyl, and R$_4$=(CH$_2$)$_6$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (62.002 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, R$^1$=(CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 96%, $\eta_{red}$=1.41 dL/g. Biodegradation (weight loss in %) at 37° C. after 120 h in phosphate buffer (pH 7.4):~0% in pure buffer, 12% in the buffer with α-chymotrypsin (4 mg/10 mL of buffer), and 38% in the buffer with lipase (4 mg/10 mL of buffer).

EXAMPLE 10

Preparation of co-poly-{[N,N'-sebacoyl-bis-(L-leucine)-1,8-octylene diester]}$_{0.90}$-{[N,N'-sebacoyl-L-lysine benzyl ester]$_{0.10}$} (10) (compound of formula (VII) wherein m=0.90, p=0.10, R$_1$=(CH$_2$)$_8$, R$_2$=Bz, R$_3$=iso-butyl, and R$_4$=(CH$_2$)$_8$).

Dry triethylamine (30.8 mL, 0.22 mole) was added to the mixture of the di-p-toluenesulfonic acid salt of bis-(L-leucine)-1,8-octylene diester (III, R$^4$=(CH$_2$)$_8$) (64.526 g, 0.0090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, R$^1$=(CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 97%, $\eta_{red}$=1.50 dL/g. Tg 27.5° C. (DSC).

EXAMPLE 11

Preparation of co-poly-{[N,N'-sebacoyl-bis-(L-leucine)-1,12-dodecylene diester]}$_{0.90}$-{[N,N'-sebacoyl-L-lysine benzyl ester]$_{0.10}$} (11) (compound of formula (VII) wherein m=0.90, p=0.10, R$_1$=(CH$_2$)$_8$, R$_2$=Bz, R$_3$=iso-butyl, and R$_4$=(CH$_2$)$_{12}$).

Dry triethylamine (30.8 mL, 0.22 mole) was added to the mixture of the di-p-toluenesulfonic acid salt of bis-(L- leucine)-1,12-dodecylene diester (III, $R^4=(CH_2)_{12}$) (69.576 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, $R^1=(CH_2)_8$) (44.444 g, 0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification, yield is 96% up to negative test on p-nitrophenol and p-toluenesulfonic acid (see below), $\eta_{red}$=0.68 dL/g.

EXAMPLE 12

Preparation of co-poly-{[N,N'-dodecyldicarboxyloyl-bis-(L-leucine)-1,6-hexylene diester]}$_{0.90}$-{[N,N'-dodecyldicarboxyloyl-L-lysine benzyl ester]$_{0.10}$} (12) (compound of formula (VII) wherein m=0.90, p=0.10, $R_1$=$(CH_2)_{12}$, $R_2$=Bz, $R_3$=iso-butyl, and $R_4$=$(CH_2)_6$.

Dry triethylamine (30.8 mL, 0.22 mole) was added to the mixture of the di-p-toluenesulfonic acid salt of bis-(L-leucine)-1,6-hexylene diester (III, $R^4=(CH_2)_6$) (62.002 g, 0.090 mole), the di-p-toluenesulfonic acid salt of L-lysine benzyl ester (IV) (5.807 g, 0.010 mole (total amount of (III)+(IV)=0.1 mole), and di-p-nitrophenyl dodecyldicarboxylate (V, $R^1=(CH_2)_{12}$) (50.055 g, 0.1 mole) in dry N,N-dimethylacetamide (DMA) (52.5 mL) (total volume of DMA and $NEt_3$ in 83.3 mL, concentration 1.2 mol/L by (III)+(IV) or by (V)) at room temperature. Afterwards the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at 30° C. under reduced pressure. After final purification yield is 96% up to negative test on p-nitrophenol and p-toluenesulfonic acid (see below), $\eta_{red}$=1.18 dL/g.

Preparation of Co-PEURs:

EXAMPLE 13

Preparation of co-poly-{[N,N'-trimethylenedioxydicarbonyl-bis-(L-leucine)-1,4-butylene diester]}$_{0.75}$-{[N,N'-trimethylenedioxydicarbonyl-L-lysine benzyl ester]$_{0.25}$} (13) (compound of formula (XI) wherein m=0.75, p=0.25, $R_2$=Bz, $R_3$=iso-butyl, $R_4$=$(CH_2)_4$, and $R_6$=$(CH_2)_3$.

Dry triethylamine (30.8 mL, 0.22 mole) was added to the mixture of the di-p-toluenesulfonic acid salt of bis-(L-leucine)-1,4-butylene diester (III, $R^4=(CH_2)_4$) (49.565 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_3$) (40.624 g, 0.1 mole) in dry N,N-dimethylacetamide (DMA) (52.5 mL) (total volume of DMA and $NEt_3$ in 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at 30° C. under reduced pressure. After final purification up to negative test on p-nitrophenol and p-toluenesulfonic acid (see below) yield is 63%, $\eta_{red}$=0.32 dL/g.

EXAMPLE 14

Preparation of co-poly-{[N,N'-(3-oxapentylene-1,5-dioxydicarbonyl)-bis-(L-leucine)-1,4-butylene diester]}$_{0.75}$-{[N,N'-(3-oxapentylene-1,5-dioxydicarbonyl)-L-lysine benzyl ester]$_{0.25}$} (14) (compound of formula (XI) wherein m=0.75, p=0.25, $R_2$=Bz, $R_3$=iso-butyl, $R_4$=$(CH_2)_4$, and $R_6$=$(CH_2)_2$—O—$(CH_2)_2$).

Dry triethylamine (30.8 mL, 0.22 mole) was added to the mixture of the di-p-toluenesulfonic acid salt of bis-(L-leucine)-1,4-butylene diester (III, $R^4=(CH_2)_4$) (49.565 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_2$—O—$(CH_2)_2$) (43.633 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure After final purification up to negative test on p-nitrophenol and p-toluenesulfonic acid (see below) yield is 78%, $\eta_{red}$=0.58 dL/g. Biodegradation (weight loss in %) at 37° C. after 240 h in phosphate buffer (pH 7.4): 4.7% in pure buffer, 2.2% in the buffer with α-chymotrypsin (4 mg/10 mL, of buffer), 4.4% in the buffer with lipase (4 mg/10 mL of buffer). Films with d=4 cm and m=500±50 mg on Teflon backing.

EXAMPLE 15

Preparation of co-poly-{[N,N'-trimethylenedioxydicarbonyl-bis-(L-leucine)-1,6-hexylene diester]}$_{0.75}$-{[N,N'-trimethylenedioxydicarbonyl-L-lysine benzyl ester]$_{0.25}$} (15) (compound of formula (XI) wherein m=0.75, p=0.25, n=112, $R_2$=Bz, $R_3$=iso-butyl, $R_4$=$(CH_2)_6$, and $R_6$=$(CH_2)_3$.

Dry triethylamine (30.8 mL, 0.22 mole) was added to the mixture of the di-p-toluenesulfonic acid salt of bis-(L-leucine)-1,6-hexylene diester (III, $R^4=(CH_2)_6$) (51.668 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_3$) (40.624 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure, After final purification up to negative test on p-nitrophenol and p-toluenesulfonic acid (see below) yield is 60%, $\eta_{red}$=0.53 dL/g. Mw=50,000, Mn=29,900, $M_w/M_n$=1.68 (GPC). Biodegradation (weight loss in %) at 37° C. after 180 h in phosphate buffer (pH 7.4): 5.0% in pure buffer, 7.3% in the buffer with α-chymotrypsin (4 mg/10 mL of buffer), and 8.2% in the buffer with lipase (4 mg/10 mL of buffer). Films with d=4 cm and m=500±50 mg on Teflon backing.

EXAMPLE 16

Preparation of co-poly-{[N,N'-(3-oxapentylene-1,5-dioxydicarbonyl)-bis-(L-leucine)-1,6-hexylene diester]}$_{0.75}$-{[N,N'-(3-oxapentylene-1,5-dioxydicarbonyl)-

L-lysine benzyl ester]$_{0.25}$} (16) (compound of formula (XI) wherein m=0.75, p=0.25, n=130, R$_2$=Bz, R$_3$=iso-butyl, R$_4$=(CH$_2$)$_6$, and R$_6$=(CH$_2$)$_2$—O—(CH$_2$)$_2$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (51.668 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) (R$^6$=(CH$_2$)$_2$—O—(CH$_2$)$_2$) (43.633 g, 0.1 mole) in dry N,N-dimethylacetamide (DMA) (52.5 mL) (total volume of DMA and NEt$_3$ is 83.3 mL, concentration 1.2 mol/L by (III)+(IV) or by (X)) at room temperature.

Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 68%, $\eta_{red}$=0.72 dL/g. Mw=61,900, Mn=38,500, Mw/Mn=1.61 (GPC). Biodegradation (weight loss in %) at 37° C. after 180 h in phosphate buffer (pH 7.4): 4.0% in pure buffer, 5.6% in the buffer with α-chymotrypsin (4 mg/10 mL of buffer), and 8.9% in the buffer with lipase (4 mg/10 mL of buffer). Films with d=4 cm and m=500±50 mg on Teflon backing.

EXAMPLE 17

Preparation of co-poly-{[N,N'-(3-oxapentylene-1,5-dioxydicarbonyl)-bis-(L-leucine)-1,6-hexylene diester]}$_{0.50}$-{[N,N'-(3-oxapentylene-1,5-dioxydicarbonyl)-L-lysine benzyl ester]$_{0.50}$} (17) (compound of formula (XI) wherein m=0.50, p=0.50, n=85, R$_2$=Bz, R$_3$=iso-butyl, R$_4$=(CH$_2$)$_6$, and R$_6$=(CH$_2$)$_2$—O—(CH$_2$)$_2$).

Dry triethylamine (30.8 mL, 0.22 mole) was added to the mixture of di-p-toluenesulfonic acid salt of bis-(L-leucine)-1,6-hexylene diester (III, R$^4$=(CH$_2$)$_6$) (34.446 g, 0.050 mole), the di-p-toluenesulfonic acid salt of L-lysine benzyl ester (IV) (29.036 g, 0.050 mole) (total amount of (III)+(IV)=0.1 mole), and active bis-carbonate (X) (R$^6$=(CH$_2$)$_2$—O—(CH$_2$)$_2$) (43.633 g, 0.1 mole) in dry N,N-dimethylacetamide (DMA) (52.5 mL) (total volume of DMA and NEt$_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 80%, $\eta_{red}$=0.45 dL/g. M$_w$=37,900, M$_n$=22,300, Mw/Mn=1.70 (GPC).

EXAMPLE 18

Preparation of co-poly-{[N,N'-(3-oxapentylene-1,5-dioxydicarbonyl)-bis-(L-leucine)-1,6-hexylene diester]}$_{0.90}$-{[N,N'-(3-oxapentylene-1,5-dioxydicarbonyl)-L-lysine benzyl ester]$_{0.10}$} (18) (compound of formula (XI) wherein m=0.90, p=0.10, n=115, R$_2$=Bz, R$_3$=iso-butyl, R$_4$=(CH$_2$)$_6$, and R$_6$=(CH$_2$)$_2$—O—(CH$_2$)$_2$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (62.002 g, 0.90 mole), the di-p-toluenesulfonic acid salt of L-lysine benzyl ester (IV) (5.807 g, 0.025 mole) (total amount of (III)+(IV)=0.1 mole), and active bis-carbonate (X) (R$^6$=(CH$_2$)$_2$—O—(CH$_2$)$_2$) (43.633 g, 0.1 mole) in dry N,N-dimethylacetamide (DMA) (52.5 mL) (total volume of DMA and NEt$_3$ is 83.3 mL, concentration 1.2 mol/L by (III)+(IV) or by (X)) at room temperature.

Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 70%, $\eta_{red}$=0.74 dL/g. M$_w$=56,500, M$_n$=33,700, M$_w$/M$_n$=1.68 (GPC).

EXAMPLE 19

Preparation of co-poly-{[N,N'-trimethylenedioxydicarbonyl-bis-(L-leucine)-1,8-octylene diester]}$_{0.75}$-{[N,N'-trimethylenedioxydicarbonyl-L-lysine benzyl ester]$_{0.25}$} (19) (compound of formula (XI) wherein m=0.75, p=0.25, R$_2$=Bz, R$_3$=iso-butyl, R$_4$=(CH$_2$)$_8$), and R$_6$=(CH$_2$)$_3$.

Dry triethylamine (30.8 mL, 0.22 mole) was added to the mixture of the di-p-toluenesulfonic acid salt of bis-(L-leucine)-1,8-octylene diester (III, R$^4$=(CH$_2$)$_8$) (53.772 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) (R$^6$=(CH$_2$)$_3$) (40.624 g, 0.1 mole) in dry N,N-dimethylacetamide (DMA) (52.5 mL) (total volume of DMA and NEt$_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 84%, $\eta_{red}$=0.46 dL/g. Biodegradation (weight loss in %) at 37° C. after 240 h in phosphate buffer (pH 7.4): 0.9% in pure buffer, 2.0% in the buffer with α-chymotrypsin (4 mg/10 mL of buffer), and 3.7% in the buffer with lipase (4 mg/10 mL of buffer). Films with d=4 cm and m=500±50 mg on Teflon backing.

EXAMPLE 20

Preparation of co-poly-{[N,N'-(3-oxapentylene-1,5-dioxydicarbonyl)-bis-(L-leucine)-1,8-octylene diester]}$_{0.75}$-{[N,N'-(3-oxapentylene-1,5-dioxydicarbonyl)-L-lysine benzyl ester]$_{0.25}$} (20) (compound of formula (XI) wherein m=0.75, p=0.25, R$_2$=Bz, R$_3$=iso-butyl, R$_4$=(CH$_2$)$_8$), and R$_6$=(CH$_2$)$_2$—O—(CH$_2$)$_2$).

Dry triethylamine (30.8 mL, 0.22 mole) was added to the mixture of the di-p-toluenesulfonic acid salt of bis-(L-leucine)-1,8-octylene diester (III, R$^4$=(CH$_2$)$_8$) (53.772 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) (R$^6$=(CH$_2$)$_2$—O—(CH$_2$)$_2$)(43.63 g, 0.1 mole) in dry N,N-dimethylacetamide (DMA) (52.5 mL) (total volume of DMA and NEt$_3$ is 83.3 mL, concentration 1.2 mol/L by (III)+(IV) or by (X)) at room temperature. Afterwards the temperature of the reaction mixture was increased to about 80° C. and stirred for 16 hours. The viscous reaction solution was cooled to room temperature, and poured into water. The separated polymer was thoroughly washed with water, dried at about 30° C. under reduced pressure. After final purification, yield is 76% up to negative test on p-nitrophenol and p-toluenesulfonic acid (see below), $\eta_{red}$=0.42 dL/g.

EXAMPLE 21

Preparation of co-poly-{[N,N'-(3-oxapentylene-1,5-dioxydicarbonyl)-bis-(L-leucine)-1,8-octylene diester]}$_{0.90}$-{[N,N'-(3-oxapentylene-1,5-dioxydicarbonyl)-L-lysine benzyl ester]$_{0.10}$} (21) (compound of formula (XI) wherein m=0.90, p=0.10, $R_2$=Bz, $R_3$=iso-butyl, $R_4$=$(CH_2)_8$) and $R_6$=$(CH_2)_2$—O—$(CH_2)_2$).

Dry triethylamine (30.8 mL, 0.22 mole) was added to the mixture of the di-p-toluenesulfonic acid salt of bis-(L-leucine)-1,8-octylene diester (III, $R^4$=$(CH_2)_8$) (64.5264 g, 0.09 mole), the di-p-toluenesulfonic acid salt of L-lysine benzyl ester (IV) (5.8072 g, 0.01 mole) (total amount of (III)+(IV)=0.1 mole), and active bis-carbonate (X) ($R^6$=$(CH_2)_2$—O—$(CH_2)_2$)(43.63 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards the temperature of the reaction mixture was increased to about 80° C. and stirred for 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 63%, $\eta_{red}$=0.51 dL/g.

EXAMPLE 22

Deprotection of Polymeric Benzyl Esters (general procedure)

According to the general procedure described herein for the preparation of coPEAs and coPEURs, the polymers were obtained as the benzyl ester forms. For the preparation of the corresponding polymers having free COOH groups, these polymers having the benzyl esters were subjected to catalytic debenzylation using hydrogen ($H_2$) gas and palladium (Pd) black as a catalyst. Suitable reaction conditions are available, e.g., in T. W. Greene, *Protecting Groups In Organic Synthesis*; Wiley: New York, 1981; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein.

(A.) Deprotection of Polymeric Benzyl Esters (coPEAs)

Palladium black catalyst (3.0 g) was added to a solution of the polymer (benzyl ester form) (10 g) in ethanol (100 mL), and dry gaseous hydrogen was bubbled through the solution for about 10 hours to about 20 hours. A magnetic stirrer was used to agitate the solution. After catalytic hydrogenolysis was complete, the reaction mixture was filtered, and clear and colorless solutions were obtained.

(B.) Deprotection of Polymeric Benzyl Esters (coPEURs)

Palladium black catalyst (3.0 g) was added to a solution of the polymer (benzyl ester form) (10 g) in ethyl acetate (100 mL), and dry gaseous hydrogen was bubbled through the solution for about 10 hours to about 30 hours. A magnetic stirrer was used to agitate the solution. After catalytic hydrogenolysis was complete, the reaction mixture was filtered, and clear and colorless solutions were obtained.

After deprotection of the polymers, no substantial change of molecular weight or polydispersity was observed. For example, for the compound (2) from Table 3 (i.e., benzyl ester form) the molecular weight characteristics were as follows: Mw=31.300, Mn=21.000, Mw/Mn=1.49. After hydrogenolysis, molecular weight characteristics are: Mw=40.900, Mn=28.000, and Mw/Mn=1.46.

EXAMPLE 23

Purification of the Benzyl Ester Polymers (General procedures)

After the polymers were precipitated in water and thoroughly washed with water, the solvent (DMA) and p-toluenesulfonic acid salt of triethylamine were removed (nearly to completion). However, the polymers still contain a significant amount of by-product of the polycondensation (e.g., p-nitrophenol) which was removed as described below.

(A.) Purification of coPEAs

The polymer obtained above (10 g) was dissolved in ethanol (50 mL, 95%). The solution was filtered and the polymer was precipitated in ethyl acetate (1.0 L), where it separates as tar like mass, and was kept overnight in refrigerator. The ethyl acetate was removed and a fresh portion of ethyl acetate (1.0 L) was added to the tar like mass and kept overnight in refrigerator again. This procedure was repeated until a negative test on p-nitrophenol (see below) was obtained. Normally it was repeated for 1–2 times. After such a treatment, p-nitrophenol (which is more soluble in ethylacetate than in water), was nearly completely removed from the polymers. The obtained tar like mass was dried, dissolved in 95% ethanol, precipitated in distilled water as a rubber-like mass, and dried at about 60° C. under reduced pressure. Yields of purified coPEAs were up to about 97%.

(B.) Purification of coPEURs

The polymer obtained above (10 g) was dissolved in chloroform (100 mL), cast as a thin film onto a cylindrical glass vessel's (d=400–500 mm) inner surface, dried at room temperature, thoroughly washed with water, and dried again. The film obtained was dissolves in dimethylformamide (DMF), and the polymer was precipitated in water. A rubber-like polymer was collected and dried at about 35° C. to about 40° C. under reduced pressure. This procedure was repeated for several times, until a negative test on p-nitrophenol was obtained (see below). Normally it was repeated about 3–4 times. After such a treatment, the yields of coPEURs decreased to ≦80%, however the viscosities increased, which is believed to be the result of the loss of low-molecular-weight fractions.

(C.) Purification of Deprotected Polymers (polyacids)

After deprotection, polymers were purified by precipitation from an ethanol solution in water. A rubber-like mass was collected and dried at room temperature under reduced pressure.

EXAMPLE 25

4-AminoTEMPO Attachment and its Biodegradation and Free Radicals Release Study

For this study the co-PEA of the following structure was chosen:

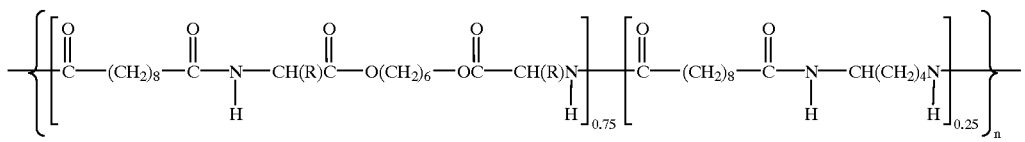

(The hydrogenolysis product of the Example 2) which revealed excellent elasticity (elongation at break ca. 1000%) and was used in in vivo "stent experiments".

4-AminoTEMPO (TAM) was attached to this polyacid using carbonyldiimidazol ($Im_2CO$) as a condensing agent. In typical procedure 1 g of polyacid was dissolved in 10 mL of purified, freshly distilled chloroform. A molar equivalent of carbonyldiimidazole was added at room temperature and stirred. A molar equivalent of TAM was added, stirred for 4 h, and kept at r. t. overnight. The solution was filtered and cast onto a hydrophobic surface. Chloroform was evaporated to dryness. The obtained film was thoroughly washed with distilled water and dried under reduced pressure at r. t. An elastic, light red-brown film was obtained. The degree of TAM attachment was 90–95%, determined by UV spectrophotometry in ethanol solution at 250 nm (Polymer does not absorb at this wavelength).

After TAM attachment, the polymer retained elastic properties. It degraded by lipase according to nearly zero order biodegradation kinetics (that is ideal for drug controlled release devices) while retaining the film's integrity whereas the starting polyacid completely degraded and/or disintegrated within 48 h in slightly alkaline buffer solution in the presence of lipase). TAM attached polymer is designated as GJ-2(TAM).

For the biodegradation study, the film of GJ-2(TAM) was obtained, it was dissolved in 10 mL of chloroform, and a Teflon disk of d=4 cm was covered by this solution for several times and evaporated so that the weight of dried polymeric coating was ca. 500 mg. The disc was placed in a lipase solution (4 mg of the enzyme in 10 mL of phosphate buffer with pH 7.4. 6 mL of the enzyme was dissolved in 15 mL of the buffer—10 mL was used for biodegradation experiment, 5 mL—for the compensation in UV measurements) and placed in thermostat at 37° C. The enzyme solution was changed every 24 h. Every 24 h the film was removed, dried with filer paper and weighed. The buffer solution was analyzed by UV-spectroscopy at 250 nm since the polymeric degradation products don't absorb at this wavelength. The same solution of the enzyme was used for the compensation.

The obtained results indicate that both biodegradation (weight loss) of the polymer and TAM releasing are very close to zero order kinetics.

Since the amide bond through which the TAM is attached to the polymer is rather stable under the biodegradation conditions, it is expected that TAM is released to the polymeric debris. At the same time the calibration curve of TAM in buffer was used for quantitative measurements. Therefore, the amount of TAM (in mg), determined by UV-spectroscopy, corresponds to the free TAM in mg (in mg/equivalent).

After 216 h (9 days) biodegradation polymer lost ca. 11% of the weight, and ca. 8% of the attached TAM was released. This, along with biodegradation and TAM releasing profiles, indicates that the TAM releasing is determined by the erosion of the polymeric film.

The results of the biodegradation (weight loss in $mg/cm^2$) of 4-AmimoTEMPO (TAM), attached to a co-PEA of the present invention, and the kinetics of nitroxyl radical release from 4-AminoTEMPO (TAM), attached to a co-PEA of the present invention, are shown in the charts below. Chart 1 illustrates the biodegradation (weight loss in $mg/cm^2$) of 4-Amino TEMPO (TAM) attached to a representative compound of the present invention. Chart 2 illustrates the kinetics of nitroxyl radical release from 4-Amino TEMPO (TAM) attached to a representative compound of the present invention.

| Time hours | weight loss $mg/cm^2$ |
|---|---|
| 0 | 0 |
| 24 | 0.22 |
| 48 | 0.47 |
| 72 | 0.85 |
| 120 | 1.5 |
| 144 | 1.71 |
| 168 | 1.85 |
| 192 | 2.23 |
| 216 | 2.42 |

CHART 1

Lipase catalyzed biodegradation (weight loss in $mg/cm_2$) of TAM-attached co-PEA [GJ-2(TAM)]

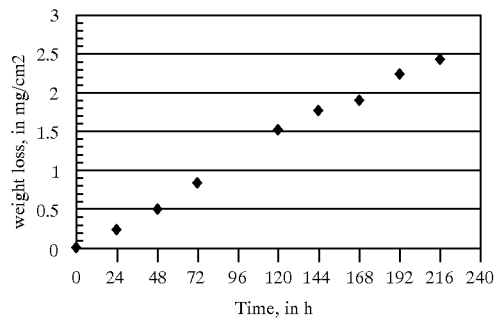

| Time hours | Nitroxy radical released mg equivalents of TAM |
|---|---|
| 0 | 0 |
| 24 | 0.95 |
| 48 | 1.4 |
| 96 | 1.93 |
| 120 | 2.2 |
| 144 | 2.5 |
| 168 | 2.97 |
| 192 | 3.2 |
| 216 | 3.7 |

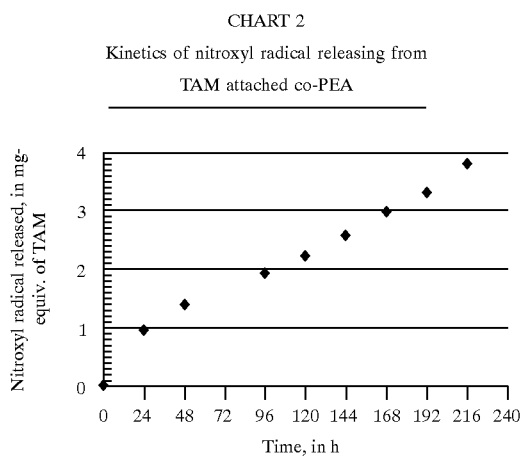

CHART 2
Kinetics of nitroxyl radical releasing from TAM attached co-PEA

EXAMPLE 24

Test on Purity (general procedure)

The coPEA or coPEUR (200–250 mg) was dissolved in a boiling 10% water solution of NaOH (5.0 mL), and the resulting solution was analyzed using UV-VIS spectrophotometer (Specord UV-VIS, Carl Zeiss, Jena, cell of 4 mL, l=1,0 cm). The absence of the absorption in the region of 250–280 nm (TosO$^-$) and at 430 nm (O$_2$NC$_6$H$_4$O$^-$) indicates that neither p-toluenesulfonic acid nor p-nitrophenol exists in the polymeric sample to any appreciable degree. It is noted that in alkaline media, p-nitrophenol does not absorb in UV region. As such, its absorption does not overlap the absorption of p-toluenesulfonic acid.

The structure of the benzylated polymers prepared in Examples 1–21 is given in the Tables below.

TABLE I

Example 25

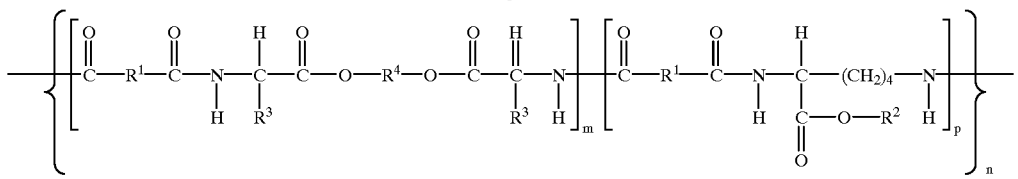

(VII)

| Compound | R$_1$ | R$_2$ | R$_3$ | R$_4$ | m | p | n |
|---|---|---|---|---|---|---|---|
| (1) | (CH$_2$)$_4$ | Bz | iso-butyl | (CH$_2$)$_6$ | 0.75 | 0.25 | 75 |
| (2) | (CH$_2$)$_8$ | Bz | iso-butyl | (CH$_2$)$_6$ | 0.75 | 0.25 | 65 |
| (3) | (CH$_2$)$_4$ | Bz | iso-butyl and Bz | (CH$_2$)$_6$ | 0.75 (0.50 + 0.25) | 0.25 | — |
| (4) | (CH$_2$)$_8$ | Bz | iso-butyl | (CH$_2$)$_6$ | 0.75 (0.50 + 0.25) | 0.25 | — |
| (5) | (CH$_2$)$_4$ | Bz | iso-butyl | (CH$_2$)$_6$ | 0.50 | 0.50 | — |
| (6) | (CH$_2$)$_8$ | Bz | iso-butyl | (CH$_2$)$_6$ | 0.50 | 0.50 | — |
| (7) | (CH$_2$)$_4$ | Bz | iso-butyl | (CH$_2$)$_8$ | 0.90 | 0.10 | — |
| (8) | (CH$_2$)$_8$ | Bz | iso-butyl | (CH$_2$)$_4$ | 0.90 | 0.10 | — |
| (9) | (CH$_2$)$_8$ | Bz | iso-butyl | (CH$_2$)$_6$ | 0.90 | 0.10 | — |
| (10) | (CH$_2$)$_8$ | Bz | iso-butyl | (CH$_2$)$_8$ | 0.90 | 0.10 | — |
| (11) | (CH$_2$)$_8$ | Bz | iso-butyl | (CH$_2$)$_{12}$ | 0.90 | 0.10 | — |
| (12) | (CH$_2$)$_{12}$ | Bz | iso-butyl | (CH$_2$)$_6$ | 0.90 | 0.10 | — |

TABLE II

Example 26

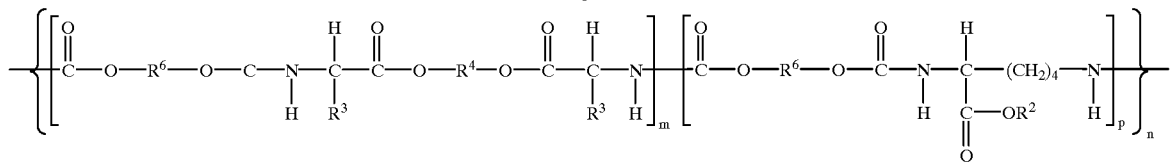

(XI)

| Compound | R$_2$ | R$_3$ | R$_4$ | R$_6$ | m | p | n |
|---|---|---|---|---|---|---|---|
| (13) | Bz | iso-butyl | (CH$_2$)$_4$ | (CH$_2$)$_3$ | 0.75 | 0.25 | — |
| (14) | Bz | iso-butyl | (CH$_2$)$_4$ | (CH$_2$)$_2$—O—(CH$_2$)$_2$ | 0.75 | 0.25 | — |
| (15) | Bz | iso-butyl | (CH$_2$)$_6$ | (CH$_2$)$_3$ | 0.75 | 0.25 | 112 |
| (16) | Bz | iso-butyl | (CH$_2$)$_6$ | (CH$_2$)$_2$—O—(CH$_2$)$_2$ | 0.75 | 0.25 | 130 |
| (17) | Bz | iso-butyl | (CH$_2$)$_6$ | (CH$_2$)$_2$—O—(CH$_2$)$_2$ | 0.50 | 0.50 | 85 |
| (18) | Bz | iso-butyl | (CH$_2$)$_6$ | (CH$_2$)$_2$—O—(CH$_2$)$_2$ | 0.90 | 0.10 | 115 |

TABLE II-continued

Example 26

$$\left\{\left[\begin{array}{c}O \\ \| \\ C\end{array}-O-R^6-O-\begin{array}{c}H \\ | \\ C\end{array}-\begin{array}{c}O \\ \| \\ N-C \\ | \\ H \end{array}\begin{array}{c} \\ C \\ | \\ R^3\end{array}-O-R^4-O-\begin{array}{c}O \\ \| \\ C\end{array}-\begin{array}{c}H \\ | \\ C \\ | \\ R^3\end{array}-\begin{array}{c} \\ N \\ | \\ H\end{array}\right]_m \left[\begin{array}{c}O \\ \| \\ C\end{array}-O-R^6-O-\begin{array}{c}O \\ \| \\ C\end{array}-\begin{array}{c}H \\ | \\ N-C \\ | \\ H\end{array}\begin{array}{c} \\ C-(CH_2)_4 \\ | \\ C-OR^2 \\ \| \\ O\end{array}-\begin{array}{c} \\ N \\ | \\ H\end{array}\right]_p\right\}_n$$

(XI)

| Compound | R₂ | R₃ | R₄ | R₆ | m | p | n |
|---|---|---|---|---|---|---|---|
| (19) | Bz | iso-butyl | (CH₂)₈ | (CH₂)₃ | 0.75 | 0.25 | — |
| (20) | Bz | iso-butyl | (CH₂)₈ | (CH₂)₂—O—(CH₂)₂ | 0.75 | 0.25 | — |
| (21) | Bz | iso-butyl | (CH₂)₈ | (CH₂)₂—O—(CH₂)₂ | 0.90 | 0.10 | — |

TABLE III

The physical properties of the polymers prepared in Examples 1–12 are given in Table III.

Example 27

| Compound | Yield (%) | $\eta_{red}$(dL/g) | Mw | Mn | Mw/Mn (GPC in THF) | B.W.L. (%)[1] | B.W.L. (%)[2] | B.W.L. (%)[3] | Tg (DSC) |
|---|---|---|---|---|---|---|---|---|---|
| (1) | 90 | 1.30 | 32,100 | 27,000 | 1.19 | | | | |
| (2) | 91 | 1.40 | 31,300 | 21,000 | 1.49 | ~0 | 1–2 | 1–2 | |
| (3) | 94 | 1.40 | | | | ~0 | 10 | 35 | |
| (4) | 95 | 0.77 | | | | | | | 20.6° C. |
| (5) | 93 | 1.25 | | | | | | | |
| (6) | 95 | 1.31 | | | | | | | |
| (7) | 94 | 1.21 | | | | | | | |
| (8) | 95 | 1.28 | | | | | | | |
| (9) | 96 | 1.41 | | | | ~0 | 12 | 38 | |
| (10) | 97 | 1.50 | | | | | | | 27.5° C. |
| (11) | 96 | 0.68 | | | | | | | |
| (12) | 96 | 1.18 | | | | | | | |
| (13) | 63 | 0.32 | | | | | | | |
| (14) | 78 | 0.58 | | | | 4.7[4] | 2.2[5] | 4.4[6] | |
| (15) | 60 | 0.53 | 50,000 | 29,900 | 1.68 | 5.0[7] | 7.3[8] | 8.2[9] | |
| (16) | 68 | 0.72 | 61,900 | 38,500 | 1.61 | 0.4[7] | 5.6[8] | 8.9[9] | |
| (17) | 80 | 0.45 | 37,900 | 22,300 | 1.70 | | | | |
| (18) | 70 | 0.74 | 56,500 | 33,700 | 1.68 | | | | |
| (19) | 84 | 0.46 | | | | 0.9[4] | 2.0[5] | 3.7[6] | |
| (20) | 76 | 0.42 | | | | | | | |
| (21) | 63 | 0.51 | | | | | | | |

[1]B.W.L. (%) is biodegradation (weight loss %) at 37° C. after 120 h in phosphate buffer (pH 7.4).
[2]B.W.L. (%) is biodegradation (weight loss %) at 37° C. after 120 h in phosphate buffer (pH 7.4) with α-chymotrypsin (4 mg/10 mL of buffer).
[3]B.W.L. (%) is biodegradation (weight loss %) at 37° C. after 120 h in phosphate buffer (pH 7.4) with lipase (4 mg/10 mL of buffer).
[4]B.W.L. (%) is biodegradation (weight loss %) at 37° C. after 240 h in phosphate buffer (pH 7.4).
[5]B.W.L. (%) is biodegradation (weight loss %) at 37° C. after 240 h in phosphate buffer (pH 7.4) with α-chymotrypsin (4 mg/10 mL of buffer).
[6]B.W.L. (%) is biodegradation (weight loss %) at 37° C. after 240 h in phosphate buffer (pH 7.4) with lipase (4 mg/10 mL of buffer).
[7]B.W.L. (%) is biodegradation (weight loss %) at 37° C. after 180 h in phosphate buffer (pH 7.4).
[8]B.W.L. (%) is biodegradation (weight loss %) at 37° C. after 180 h in phosphate buffer (pH 7.4) with α-chymotrypsin (4 mg/10 mL of buffer).
[9]B.W.L. (%) is biodegradation (weight loss %) at 37° C. after 180 h in phosphate buffer #H 7.4) with lipase (4 mg/10 mL of buffer).

The benzylated polymers obtained had high Mw in the range 30,000–60,000 and narrow polydispersity—Mw/Mn= 1.2–1.7 (Determined by GPC for the polymers, soluble in THF), and possess excellent film-forming properties. They revealed rather low glass transition temperature (Tg=9–20° C.). The polymers are soluble in common organic solvents like chloroform (all of them), ethanol, (copoly(ester amide) s), ethylacetate (copoly(ester urethane)s), some of them in THF. Both co-PEAs and co-PEURs reveal rather high tendency to in vitro biodegradation. Co-PEAs are more inclined to specific (enzyme catalyzed) hydrolysis, whereas co-PEURs showed the tendency to both specific and non-specific (chemical) hydrolysis.

EXAMPLE 28

In Vitro Biodegradation Study

In vitro biodegradation studies were performed by weight loss. Standard films with d=4 cm and m=450–550 mg (pure films in case of non-contractive poly(ester amide)s and films on Teflon backing in case of contractive poly(ester urethane) s), were placed into the glass vessels containing 10 mL of 0.2 M phosphate buffer solution with pH=7.4 (either pure buffer or buffer containing 4 mg of an enzyme—α-chymotrypsin or lipase) and placed at 37° C. The films were removed from the solutions after a predetermined time, dried with filter paper and weighted. Buffer or enzyme solution was changed every 24 h.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer of formula (VII):

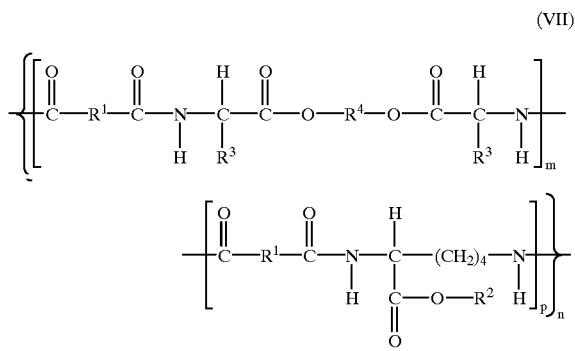

wherein m is about 0.1 to about 0.9;

p is about 0.9 to about 0.1;

n is about 50 to about 150;

each $R^1$ is independently $(C_2–C_{20})$alkyl;

each $R^2$ is independently hydrogen, or $(C_6–C_{10})$aryl$(C_1–C_6)$alkyl;

each $R^3$ is independently hydrogen, $(C_1–C_6)$alkyl, $(C_2–C_6)$alkenyl, $(C_2–C_6)$alkynyl, or $(C_6–C_{10})$aryl$(C_1–C_6)$alkyl; and each $R^4$ is independently $(C_2–C_{20})$alkyl.

2. The polymer of claim 1 wherein each $R^1$ is independently $(CH_2)_4$, $(CH_2)_8$, or $(CH_2)_{12}$.

3. The polymer of claim 1 wherein each $R^2$ is independently hydrogen or benzyl.

4. The polymer of claim 1 wherein each $R^3$ is independently iso-butyl or benzyl.

5. The polymer of claim 1 wherein each $R^4$ is independently $(CH_2)_4$, $(CH_2)_6$, $(CH_2)_8$, or $(CH_2)_{12}$.

6. The polymer of claim 1 wherein p/(p+m) is about 0.9 to about 0.1.

7. The polymer of claim 1 wherein m/(p+m) Is about 0.1 to about 0.9.

8. A polymer of formula (VII) comprising one or more subunits of the formula (I):

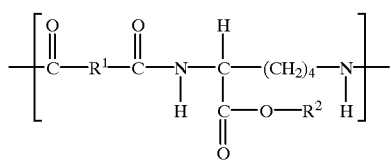

wherein $R^1$ is independently $(C_2–C_{20})$alkyl; and $R^2$ is independently hydrogen, or $(C_6–C_{10})$aryl$(C_1–C_6)$alkyl;

and one or more subunits of the formula (II):

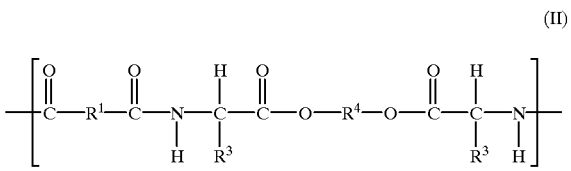

wherein each $R^3$ is independently hydrogen, $(C_1–C_6)$alkyl, $(C_2–C_6)$alkenyl, $(C_2–C_6)$alkynyl, or $(C_6–C_{10})$aryl$(C_1–C_6)$alkyl; and $R^4$ is independently $(C_2–C_{20})$alkyl.

9. The polymer of claim 8 wherein $R^1$ is independently $(CH_2)_4$, $(CH_2)_8$, or $(CH_2)_{12}$.

10. The polymer of claim 8 wherein $R^2$ is independently hydrogen or benzyl.

11. The polymer of claim 8 wherein each $R^3$ is independently iso-butyl or benzyl.

12. The polymer of claim 8 wherein $R^4$ is independently $(CH_2)_4$, $(CH_2)_6$, $(CH_2)_8$, or $(CH_2)_{12}$.

13. The polymer of claim 8 that is a polymer of formula (VII):

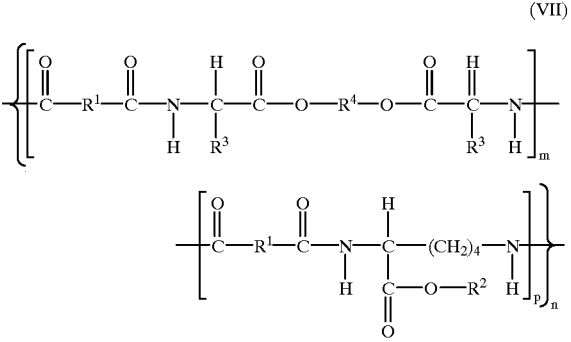

wherein m is about 0.1 to about 0.9;

p is about 0.9 to about 0.1; and n is about 50 to about 150.

14. The polymer of claim 13 wherein p/(p+m) is about 0.9 to about 0.1.

15. The polymer of claim 13 wherein m/(p+m) is about 0.1 to about 0.9.

16. A polymer of formula (VII) formed from an amount of one or more compounds of formula (III):

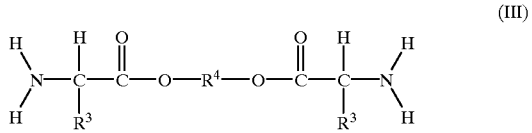

wherein each $R^3$ is independently hydrogen, $(C_1–C_6)$alkyl, $(C_2–C_6)$alkenyl, $(C_2–C_6)$alkynyl, or $(C_6–C_{10})$aryl$(C_1–C_6)$alkyl; and $R^4$ is independently $(C_2–C_{20})$alkyl; or a suitable salt thereof;

an amount of one or more compounds of formula (IV):

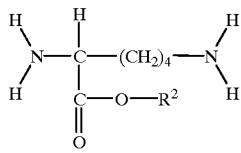
(IV)

wherein
R² is independently hydrogen, or (C₆–C₁₀)aryl(C₁–C₆)alkyl; or a suitable salt thereof; and an amount of one or more compounds of formula (V):

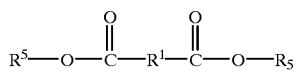
(V)

wherein
R¹ is independently (C₂–C₂₀)alkyl; and
each R⁵ is independently (C₆–C₁₀)aryl optionally substituted with one or more nitro, cyano, halo, trifluoromethyl, or trifluoromethoxy.

17. The polymer of claim 16 wherein R¹ is independently (CH₂)₄, (CH₂)₈, or (CH₂)₁₂.

18. The polymer of claim 16 wherein R² is independently hydrogen or benzyl.

19. The polymer of claim 16 wherein each R³ is independently iso-butyl or benzyl.

20. The polymer of claim 16 wherein R⁴ is independently (CH₂)₄, (CH₂)₆, (CH₂)₈, or (CH₂)₁₂.

21. The polymer of claim 16 wherein each R⁵ is p-nitrophenyl.

22. The polymer of claim 16 wherein the compound of formula (III) is the di-p-tolunesulfonic acid salt of a bis-(L-α-amino acid)-α,ω-alkylene diester.

23. The polymer of claim 16 wherein the compound of formula (IV) is the di-p-tolunesulfonic acid salt of L-lysine benzyl ester.

24. The polymer of claim 16 wherein the compound of formula (V) is di-p-nitrophenyl adipate, di-p-nitrophenyl sebacinate, or di-p-nitrophenyl dodecyldicarboxylate.

25. The polymer of claim 16 that is a polymer of formula (VII):

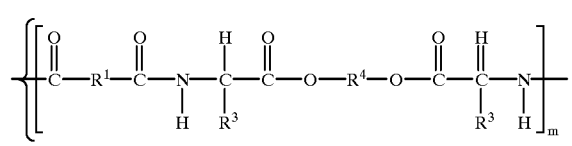
(VII)

wherein
m is about 0.1 to about 0.9;
p is about 0.9 to about 0.1; and
n is about 50 to about 150.

26. The polymer of claim 25 wherein p/(p+m) is about 0.9 to about 0.1.

27. The polymer of claim 25 wherein m/(p+m) is about 0.1 to about 0.9.

28. A method for preparing a polymer of formula (VII):

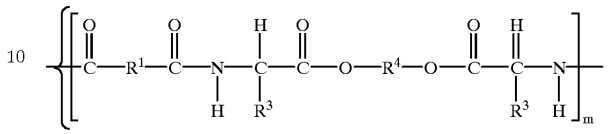
(VII)

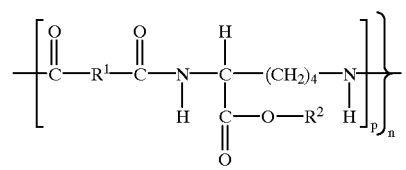

wherein
m is about 0.1 to about 0.9;
p is about 0.9 to about 0.1;
n is about 50 to about 150;
each R¹ is independently (C₂–C₂₀)alkyl;
each R² is independently hydrogen, or (C₆–C₁₀)aryl(C₁–C₆)alkyl;
each R³ is independently hydrogen, (C₁–C₆)alkyl, (C₂–C₆)alkenyl, (C₂–C₆)alkynyl, or (C₆–C₁₀)aryl(C₁–C₆)alkyl; and
each R⁴ is independently (C₂–C₂₀)alkyl;
comprising contacting an amount of one or more compounds of formula (III):

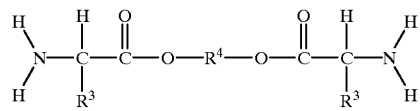
(III)

or a suitable salt thereof;
an amount of one or more compounds of formula (IV):

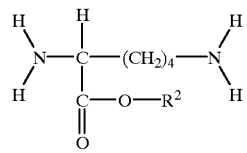
(IV)

or a suitable salt thereof; and
an amount of one or more compounds of formula (V):

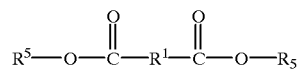
(V)

wherein
each R⁵ is independently (C₆–C₁₀)aryl optionally substituted with one or more nitro, cyano, halo, trifluoromethyl, or trifluoromethoxy;
under suitable conditions to provide the polymer of formula (VII).

29. The method of claim 28 wherein each $R^1$ is independently $(CH_2)_4$, $(CH_2)_8$, or $(CH_2)_{12}$.

30. The method of claim 28 wherein each $R^2$ is independently hydrogen or benzyl.

31. The method of claim 28 wherein each $R^3$ is independently iso-butyl or benzyl.

32. The method of claim 28 wherein each $R^4$ is independently $(CH_2)_4$, $(CH_2)_6$, $(CH_2)_8$, or $(CH_2)_{12}$.

33. The method of claim 28 wherein each $R^5$ is p-nitrophenyl.

34. The method of claim 28 wherein the compound of formula (III) is the di-p-tolunesulfonic acid salt of a bis-(L-α-amino acid)-α,ω-alkylene diester.

35. The method of claim 28 wherein the compound of formula (IV) is the di-p-tolunesulfonic acid salt of L-lysine benzyl ester.

36. The method of claim 28 wherein the compound of formula (V) is di-p-nitrophenyl adipate, di-p-nitrophenyl sebacinate, or di-p-nitrophenyl dodecyldicarboxylate.

37. The method of claim 28 wherein the contacting is carried out in the presence of a base.

38. The method of claim 37 wherein the base is triethylamine.

39. The method of claim 28 wherein the contacting is carried out in the presence of a solvent.

40. The method of claim 39 wherein the solvent is N,N-dimethylacetamide.

41. The method of claim 28 wherein the contacting is carried out at about 50° C. to about 100° C.

42. The method of claim 28 wherein the contacting occurs for about 10 hours to about 24 hours.

43. The method of claim 28 further comprising purifying the polymer of formula (VII).

44. The method of claim 28 wherein p/(p+m) is about 0.9 to about 0.1.

45. The method of claim 28 wherein m/(p+m) is about 0.1 to about 0.9.

46. A polymer of formula (XI):

49. The polymer of claim 46 wherein each $R^4$ is independently $(CH_2)_4$, $(CH_2)_6$, $(CH_2)_8$, or $(CH_2)_{12}$.

50. The polymer of claim 46 wherein each $R^6$ is independently $(CH_2)_3$ or $(CH_2)_2$—O—$(CH_2)_2$.

51. The polymer of claim 46 wherein p/(p+m) is about 0.9 to about 0.1.

52. The polymer of claim 46 wherein m/(p+m) is about 0.1 to about 0.9.

53. A polymer of formula (XI) comprising one or more subunits of the formula (VIII):

$$\left[ \begin{array}{c} \text{(VIII)} \end{array} \right]$$

wherein
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
$R^4$ is independently $(C_2-C_{20})$alkyl;
$R^6$ is independently $(C_2-C_{20})$alkyl or $(C_2-C_8)$alkyloxy$(C_2-C_{20})$alkyl; and one or more subunits of the formula (IX):

$$\left[ \begin{array}{c} \text{(IX)} \end{array} \right]$$

wherein
$R^2$ is independently hydrogen, or $(C_6-C_{10})$aryl$(C_1-C_6)$alkyl.

(XI)

wherein
m is about 0.1 to about 0.9;
p is about 0.9 to about 0.1;
n is about 50 to about 150;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
each $R^4$ is independently $(C_2-C_{20})$alkyl; and
each $R^6$ is independently $(C_2-C_{20})$alkyl or $(C_2-C_8)$alkyloxy$(C_2-C_{20})$alkyl.

47. The polymer of claim 46 wherein each $R^2$ is independently hydrogen or benzyl.

48. The polymer of claim 46 wherein each $R^3$ is independently iso-butyl or benzyl.

54. The polymer of claim 53 wherein $R^2$ is independently hydrogen or benzyl.

55. The polymer of claim 53 wherein each $R^3$ is independently iso-butyl or benzyl.

56. The polymer of claim 53 wherein $R^4$ is independently $(CH_2)_4$, $(CH_2)_6$, $(CH_2)_8$, or $(CH_2)_{12}$.

57. The polymer of claim 53 wherein $R^6$ is independently $(CH_2)_3$ or $(CH_2)_2$—O—$(CH_2)_2$.

58. The polymer of claim 53 that is a polymer of formula (XI):

(XI)

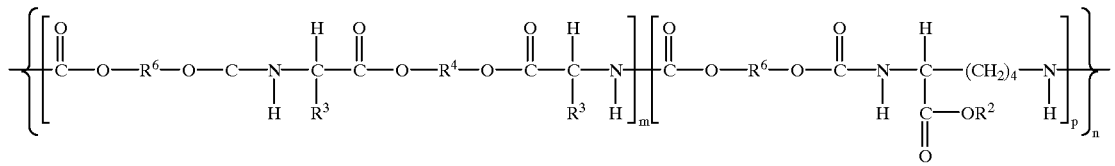

wherein
   m is about 0.1 to about 0.9;
   p is about 0.9 to about 0.1;
   n is about 50 to about 150;
   each $R^2$ is independently hydrogen, or $(C_6–C_{10})$aryl$(C_1–C_6)$alkyl;
   each $R^3$ is independently hydrogen, $(C_1–C_6)$alkyl, $(C_2–C_6)$alkenyl, $(C_2–C_6)$alkynyl, or $(C_6–C_{10})$aryl$(C_1–C_6)$alkyl;
   each $R^4$ is independently $(C_2–C_{20})$alkyl;
   each $R^5$ is independently $(C_6–C_{10})$aryl optionally substituted with one or more nitro, cyano, halo, trifluoromethyl, or trifluoromethoxy; and
   each $R^6$ is independently $(C_2–C_{20})$alkyl or $(C_2–C_8)$alkyloxy$(C_2–C_{20})$alkyl.

59. A polymer of formula (XI) formed from an amount of one or more compounds of formula (III):

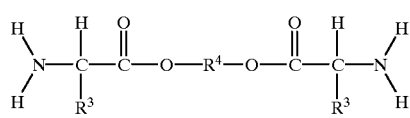

(III)

wherein
   each $R^3$ is independently hydrogen, $(C_1–C_6)$alkyl, $(C_2–C_6)$alkenyl, $(C_2–C_6)$alkynyl, or $(C_6–C_{10})$aryl$(C_1–C_6)$alkyl; and
   $R^4$ is independently $(C_2–C_{20})$alkyl; or a suitable salt thereof;
an amount of one or more compounds of formula (IV):

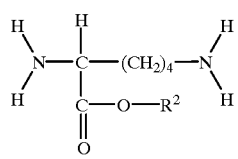

(IV)

wherein $R^2$ is independently hydrogen, or $(C_6–C_{10})$aryl$(C_1–C_6)$alkyl; or a suitable salt thereof; and an amount of one or more compounds of formula (X):

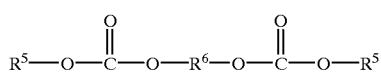

(X)

wherein each $R^5$ is independently $(C_6–C_{10})$aryl optionally substituted with one or more nitro, cyano, halo, trifluoromethyl, or trifluoromethoxy; and $R^6$ is independently $(C_2–C_{20})$alkyl or $(C_2–C_8)$alkyloxy$(C_2–C_{20})$alkyl.

60. The polymer of claim 59 wherein $R^2$ is independently hydrogen or benzyl.

61. The polymer of claim 59 wherein each $R^3$ is independently iso-butyl or benzyl.

62. The polymer of claim 59 wherein $R^4$ is independently $(CH_2)_4$, $(CH_2)_6$, $(CH_2)_8$, or $(CH_2)_{12}$.

63. The polymer of claim 59 wherein each $R^5$ is p-nitrophenyl.

64. The polymer of claim 59 wherein $R^6$ is independently $(CH_2)_3$ or $(CH_2)_2—O—(CH_2)_2$.

65. The polymer of claim 59 wherein the compound of formula (III) is the di-p-tolunesulfonic acid salt of a bis-(L-α-amino acid)-α,ω-alkylene diester.

66. The polymer of claim 59 wherein the compound of formula (IV) is the di-p-tolunesulfonic acid salt of L-lysine benzyl ester.

67. The polymer of claim 59 wherein the compound of formula (X) is 1,3-bis(4-nitro-phenoxycarbonyloxy) propane; or 2,2'-bis-4-nitrophenoxycarbonyloxy ethylether.

68. The polymer of claim 59 that is a polymer of formula (XI):

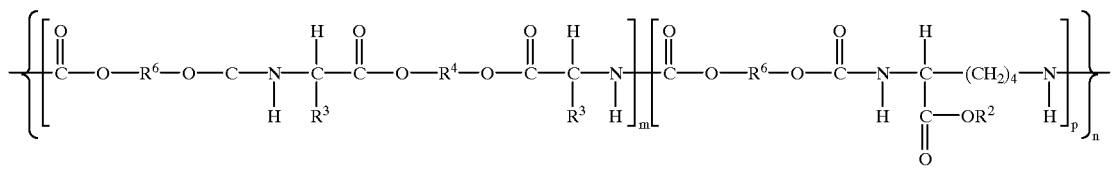

(XI)

wherein m is about 0.1 to about 0.9;
p is about 0.9 to about 0.1; and
n is about 50 to about 150.

69. The polymer of claim 68 wherein p/(p+m) is about 0.9 to about 0.1.

70. The polymer of claim 68 wherein m/(p+m) is about 0.1 to about 0.9.

71. A method for preparing a polymer of formula (XI):

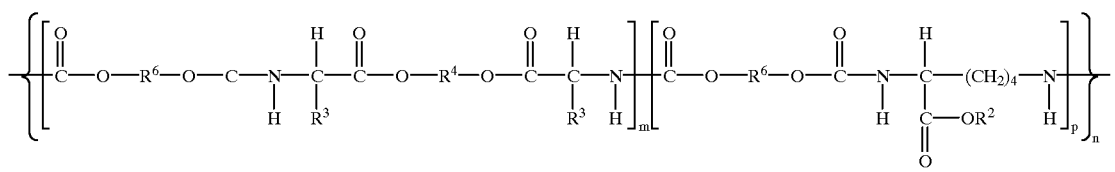

(XI)

wherein m is about 0.1 to about 0.9;
p is about 0.9 to about 0.1;
n is about 50 to about 150;
each $R^2$ is independently hydrogen, or $(C_6-C_{10})$aryl $(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl $(C_1-C_6)$alkyl;
each $R^4$ is independently $(C_2-C_{20})$alkyl;
each $R^5$ is independently $(C_6-C_{10})$aryl optionally substituted with one or more nitro, cyano, halo, trifluoromethyl, or trifluoromethoxy; and
each $R^6$ is independently $(C_2-C_{20})$alkyl or $(C_2-C_8)$alkyloxy$(C_2-C_{20})$alkyl;

comprising contacting an amount of one or more compounds of formula (III):

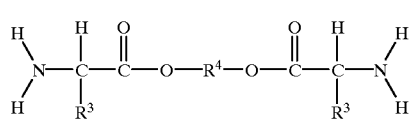

(III)

or a suitable salt thereof;

an amount of one or more compounds of formula (IV):

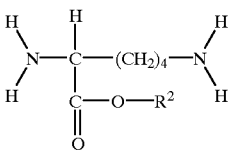

(IV)

or a suitable salt thereof; and
an amount of one or more compounds of formula (X):

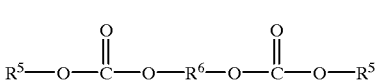

(X)

under suitable conditions to provide the polymer of formula (XI).

72. The method of claim 71 wherein each $R^2$ is independently hydrogen or benzyl.

73. The method of claim 71 wherein each $R^3$ is independently iso-butyl or benzyl.

74. The method of claim 71 wherein each $R^4$ is independently $(CH_2)_4$, $(CH_2)_6$, $(CH_2)_8$, or $(CH_2)_{12}$.

75. The method of claim 71 wherein each $R^5$ is p-nitrophenyl.

76. The method of claim 71 wherein each $R^6$ is independently $(CH_2)_3$ or $(CH_2)_2-O-(CH_2)_{12}$.

77. The method of claim 71 wherein the compound of formula (III) is the di-p-tolunesulfonic acid salt of a bis-(L-α-amino acid)-α,ω-alkylene diester.

78. The method of claim 71 wherein the compound of formula (IV) is the di-p-tolunesulfonic acid salt of L-lysine benzyl ester.

79. The method of claim 71 wherein the compound of formula (X) is 1,3-bis(4-nitro-phenoxycarbonyloxy) propane; or 2,2'-bis-4-nitrophenoxycarbonyloxy ethylether.

80. The method of claim 71 wherein the contacting is carried out in the presence of a base.

81. The method of claim 80 wherein the base is triethylamine.

82. The method of claim 71 wherein the contacting is carried out in the presence of a solvent.

83. The method of claim 82 wherein the solvent is N,N-dimethylacetamide.

84. The method of claim 71 wherein the contacting is carried out at about 50° C. to about 100° C.

85. The method of claim 71 wherein the contacting occurs for about 10 hours to about 24 hours.

86. The method of claim 71 further comprising purifying the polymer of formula (XI).

87. The method of claim 71 wherein p/(p+m) is about 0.9 to about 0.1.

88. The method of claim 71 wherein m/(p+m) is about 0.1 to about 0.9.

89. A method of using a polymer of any one of claims 1–70 for use as a medical device, a pharmaceutical, a carrier for covalent immobilization of a drug, or a bioactive substance.

90. A method of using a polymer of any one of claims 1–70 for the manufacture of a medical device, a pharmaceutical, a carrier for covalent immobilization of a drug, or a bioactive substance.

* * * * *